(12) United States Patent
Carley et al.

(10) Patent No.: US 8,202,283 B2
(45) Date of Patent: *Jun. 19, 2012

(54) METHODS FOR MANUFACTURING A CLIP AND CLIP

(75) Inventors: Michael T. Carley, San Jose, CA (US); Richard S. Ginn, Gilroy, CA (US)

(73) Assignee: Integrated Vascular Systems, Inc., Redwood City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/945,646

(22) Filed: Nov. 12, 2010

(65) Prior Publication Data
US 2011/0060355 A1 Mar. 10, 2011

Related U.S. Application Data

(60) Division of application No. 12/403,256, filed on Mar. 12, 2009, now Pat. No. 7,850,797, which is a division of application No. 10/541,083, filed as application No. PCT/US03/40812 on Dec. 17, 2003, now Pat. No. 7,854,810, which is a continuation of application No. 10/335,075, filed on Dec. 31, 2002, now Pat. No. 7,211,101.

(51) Int. Cl.
*A61B 17/08* (2006.01)
*C22F 1/00* (2006.01)
(52) U.S. Cl. ........................ 606/151; 148/563
(58) Field of Classification Search .................. 148/563, 148/402; 623/1.15–1.22; 606/151–158, 606/213–221, 911
See application file for complete search history.

(56) References Cited

U.S. PATENT DOCUMENTS

| 287,046 A | 10/1883 | Norton |
| 438,400 A | 10/1890 | Brennen |
| 1,088,393 A | 2/1914 | Backus |
| 1,331,401 A | 2/1920 | Summers |
| 1,596,004 A | 8/1926 | De Bengoa |
| 1,647,958 A | 11/1927 | Ciarlante |

(Continued)

FOREIGN PATENT DOCUMENTS
AU 2003297432 7/2004
(Continued)

OTHER PUBLICATIONS

U.S. Appl. No. 09/610,128, filed Jul. 5, 2000, Kerievsky.

(Continued)

*Primary Examiner* — Scott Kastler
*Assistant Examiner* — Vanessa Luk
(74) *Attorney, Agent, or Firm* — Workman Nydegger; Randy Shen

(57) ABSTRACT

The present disclosure relates to a clip manufactured according to a method which can be used to engage body tissue for the purpose of closing wounds. Such clips are generally annular in shape and have radially inwardly extending tines. The present disclosure first forms a precursor which, in one embodiment, has the tines extending radially outwardly from the annular body and then forms the clip by inverting the precursor such that the tines extend radially inwardly. In an alternate embodiment, the precursor is formed with an oversized lateral dimension and then compressed inwardly to bring the tines closer together and to reduce the lateral dimension of the precursor. Such clips may be manufactured from a superelastic alloy such as nickel-titanium, in which case the inverted or compressed precursor must be heated and quenched to heat set the clip in its final shape.

15 Claims, 5 Drawing Sheets

U.S. PATENT DOCUMENTS

| | | |
|---|---|---|
| 1,880,569 A | 10/1932 | Weis |
| 2,087,074 A | 7/1937 | Tucker |
| 2,254,620 A | 9/1941 | Miller |
| 2,316,297 A | 4/1943 | Southerland et al. |
| 2,371,978 A | 3/1945 | Perham |
| 2,453,227 A | 11/1948 | James |
| 2,583,625 A | 1/1952 | Bergan |
| 2,684,070 A | 7/1954 | Kelsey |
| 2,910,067 A | 10/1959 | White |
| 2,944,311 A | 7/1960 | Schneckenberger |
| 2,951,482 A | 9/1960 | Sullivan |
| 2,969,887 A | 1/1961 | Darmstadt et al. |
| 3,015,403 A | 1/1962 | Fuller |
| 3,113,379 A | 12/1963 | Frank |
| 3,120,230 A | 2/1964 | Skold |
| 3,142,878 A | 8/1964 | Santora |
| 3,209,754 A | 10/1965 | Brown |
| 3,482,428 A | 12/1969 | Kapitanov et al. |
| 3,494,533 A | 2/1970 | Green et al. |
| 3,510,923 A | 5/1970 | Blake |
| 3,523,351 A | 8/1970 | Filia |
| 3,586,002 A | 6/1971 | Wood et al. |
| 3,604,425 A | 9/1971 | Le Roy |
| 3,618,447 A | 11/1971 | Goins |
| 3,677,243 A | 7/1972 | Nerz |
| 3,757,629 A | 9/1973 | Schneider |
| 3,805,337 A | 4/1974 | Branstetter |
| 3,823,719 A | 7/1974 | Cummings |
| 3,828,791 A | 8/1974 | Santos |
| 3,856,016 A | 12/1974 | Davis |
| 3,874,388 A | 4/1975 | King et al. |
| 3,908,662 A | 9/1975 | Razgulov et al. |
| 3,926,194 A | 12/1975 | Greenberg et al. |
| 3,939,820 A | 2/1976 | Grayzel |
| 3,944,114 A | 3/1976 | Coppens |
| 3,960,147 A | 6/1976 | Murray |
| 3,985,138 A | 10/1976 | Jarvik |
| 4,007,743 A | 2/1977 | Blake |
| 4,014,492 A | 3/1977 | Rothfuss |
| 4,018,228 A | 4/1977 | Goosen |
| 4,047,533 A | 9/1977 | Perciaccante et al. |
| 4,064,881 A | 12/1977 | Meredith |
| 4,112,944 A | 9/1978 | Williams |
| 4,153,321 A | 5/1979 | Pombrol |
| 4,162,673 A | 7/1979 | Patel |
| 4,169,476 A | 10/1979 | Hiltebrandt |
| 4,192,315 A | 3/1980 | Hilzinger et al. |
| 4,201,215 A | 5/1980 | Crossett et al. |
| 4,204,541 A | 5/1980 | Kapitanov |
| 4,207,870 A | 6/1980 | Eldridge |
| 4,214,587 A | 7/1980 | Sakura, Jr. |
| 4,215,699 A | 8/1980 | Patel |
| 4,217,902 A | 8/1980 | March |
| 4,273,129 A | 6/1981 | Boebel |
| 4,274,415 A | 6/1981 | Kanamoto et al. |
| 4,278,091 A | 7/1981 | Borzone |
| 4,317,445 A | 3/1982 | Robinson |
| 4,318,401 A | 3/1982 | Zimmerman |
| 4,327,485 A | 5/1982 | Rix |
| 4,345,606 A | 8/1982 | Littleford |
| 4,368,736 A | 1/1983 | Kaster |
| 4,396,139 A | 8/1983 | Hall et al. |
| 4,411,654 A | 10/1983 | Boarini et al. |
| 4,412,832 A | 11/1983 | Kling et al. |
| 4,428,376 A | 1/1984 | Mericle |
| 4,440,170 A | 4/1984 | Golden et al. |
| 4,449,531 A | 5/1984 | Cerwin et al. |
| 4,475,544 A | 10/1984 | Reis |
| 4,480,356 A | 11/1984 | Martin |
| 4,485,816 A | 12/1984 | Krumme |
| RE31,855 E | 3/1985 | Osborne |
| 4,505,273 A | 3/1985 | Braun et al. |
| 4,505,274 A | 3/1985 | Speelman |
| 4,523,591 A | 6/1985 | Kaplan et al. |
| 4,523,695 A | 6/1985 | Braun et al. |
| 4,525,157 A | 6/1985 | Vaillancourt |
| 4,526,174 A | 7/1985 | Froehlich |
| 4,586,503 A | 5/1986 | Kirsch et al. |
| 4,592,498 A | 6/1986 | Braun et al. |
| 4,596,559 A | 6/1986 | Fleischhacker |
| 4,607,638 A | 8/1986 | Crainich |
| 4,610,251 A | 9/1986 | Kumar |
| 4,610,252 A | 9/1986 | Catalano |
| 4,635,634 A | 1/1987 | Santos |
| 4,651,737 A | 3/1987 | Deniega |
| 4,664,305 A | 5/1987 | Blake, III et al. |
| 4,665,906 A * | 5/1987 | Jervis ............................. 606/78 |
| 4,687,469 A | 8/1987 | Osypka |
| 4,693,249 A | 9/1987 | Schenck et al. |
| 4,719,917 A | 1/1988 | Barrows et al. |
| 4,724,840 A | 2/1988 | McVay et al. |
| 4,738,658 A | 4/1988 | Magro et al. |
| 4,744,364 A | 5/1988 | Kensey |
| 4,747,407 A | 5/1988 | Liu et al. |
| 4,759,364 A | 7/1988 | Boebel |
| 4,771,782 A | 9/1988 | Millar |
| 4,772,266 A | 9/1988 | Groshong |
| 4,777,950 A | 10/1988 | Kees, Jr. |
| 4,789,090 A | 12/1988 | Blake, III |
| 4,832,688 A | 5/1989 | Sagae et al. |
| 4,836,204 A | 6/1989 | Landymore et al. |
| 4,852,568 A | 8/1989 | Kensey |
| 4,860,746 A | 8/1989 | Yoon |
| 4,865,026 A | 9/1989 | Barrett |
| 4,874,122 A | 10/1989 | Froelich et al. |
| 4,878,915 A | 11/1989 | Brantigan |
| 4,887,601 A | 12/1989 | Richards |
| 4,890,612 A | 1/1990 | Kensey |
| 4,902,508 A | 2/1990 | Badylak et al. |
| 4,917,087 A | 4/1990 | Walsh et al. |
| 4,917,089 A | 4/1990 | Sideris |
| 4,929,240 A | 5/1990 | Kirsch et al. |
| 4,934,364 A | 6/1990 | Green |
| 4,950,258 A | 8/1990 | Kawai et al. |
| 4,957,499 A | 9/1990 | Lipatov et al. |
| 4,961,729 A | 10/1990 | Vaillancourt |
| 4,976,721 A | 12/1990 | Blasnik et al. |
| 4,983,176 A | 1/1991 | Cushman et al. |
| 4,997,436 A | 3/1991 | Oberlander |
| 4,997,439 A | 3/1991 | Chen |
| 5,002,562 A | 3/1991 | Oberlander |
| 5,007,921 A | 4/1991 | Brown |
| 5,015,247 A | 5/1991 | Michelson |
| 5,021,059 A | 6/1991 | Kensey et al. |
| 5,026,390 A | 6/1991 | Brown |
| 5,030,226 A | 7/1991 | Green et al. |
| 5,032,127 A | 7/1991 | Frazee et al. |
| 5,047,047 A | 9/1991 | Yoon |
| 5,053,008 A | 10/1991 | Bajaj |
| 5,059,201 A | 10/1991 | Asnis |
| 5,061,274 A | 10/1991 | Kensey |
| 5,078,731 A | 1/1992 | Hayhurst |
| 5,092,941 A | 3/1992 | Miura |
| 5,100,418 A | 3/1992 | Yoon et al. |
| 5,100,422 A | 3/1992 | Berguer et al. |
| 5,108,420 A | 4/1992 | Marks |
| 5,108,421 A | 4/1992 | Fowler |
| 5,114,032 A | 5/1992 | Laidlaw |
| 5,114,065 A | 5/1992 | Storace |
| 5,116,349 A | 5/1992 | Aranyi |
| 5,122,122 A | 6/1992 | Allgood |
| 5,122,156 A | 6/1992 | Granger et al. |
| 5,131,379 A | 7/1992 | Sewell, Jr. |
| 5,147,381 A | 9/1992 | Heimerl et al. |
| 5,156,609 A | 10/1992 | Nakao et al. |
| 5,167,634 A | 12/1992 | Corrigan, Jr. et al. |
| 5,167,643 A | 12/1992 | Lynn |
| 5,171,249 A | 12/1992 | Stefanchik et al. |
| 5,171,250 A | 12/1992 | Yoon |
| 5,176,648 A | 1/1993 | Holmes et al. |
| 5,192,288 A | 3/1993 | Thompson et al. |
| 5,192,300 A | 3/1993 | Fowler |
| 5,192,301 A | 3/1993 | Kamiya et al. |
| 5,192,302 A | 3/1993 | Kensey et al. |
| 5,192,602 A | 3/1993 | Spencer et al. |
| 5,209,756 A | 5/1993 | Seedhorn et al. |
| 5,217,024 A | 6/1993 | Dorsey et al. |

| Patent No. | Date | Inventor |
|---|---|---|
| 5,222,974 A | 6/1993 | Kensey et al. |
| 5,226,908 A | 7/1993 | Yoon |
| 5,236,435 A | 8/1993 | Sewell, Jr. |
| 5,242,456 A | 9/1993 | Nash et al. |
| 5,242,457 A | 9/1993 | Akopov et al. |
| 5,242,459 A | 9/1993 | Buelna |
| 5,243,857 A | 9/1993 | Velez |
| 5,246,156 A | 9/1993 | Rothfuss et al. |
| 5,246,443 A | 9/1993 | Mai |
| 5,250,058 A | 10/1993 | Miller et al. |
| 5,254,105 A | 10/1993 | Haaga |
| 5,269,792 A | 12/1993 | Kovac et al. |
| 5,275,616 A | 1/1994 | Fowler |
| 5,281,422 A | 1/1994 | Badylak et al. |
| 5,282,808 A | 2/1994 | Kovac et al. |
| 5,282,827 A | 2/1994 | Kensey et al. |
| 5,289,963 A | 3/1994 | McGarry et al. |
| 5,290,243 A | 3/1994 | Chodorow et al. |
| 5,290,310 A | 3/1994 | Makower et al. |
| 5,292,309 A | 3/1994 | Van Tassel et al. |
| 5,292,332 A | 3/1994 | Lee |
| 5,304,183 A | 4/1994 | Gourlay et al. |
| 5,304,184 A | 4/1994 | Hathaway et al. |
| 5,304,204 A | 4/1994 | Bregen |
| 5,306,254 A | 4/1994 | Nash et al. |
| 5,309,927 A | 5/1994 | Welch |
| 5,318,542 A | 6/1994 | Hirsch et al. |
| 5,320,639 A | 6/1994 | Rudnick |
| 5,327,908 A | 7/1994 | Gerry |
| 5,330,445 A | 7/1994 | Haaga |
| 5,334,216 A | 8/1994 | Vidal et al. |
| 5,334,217 A | 8/1994 | Das |
| 5,335,680 A | 8/1994 | Moore |
| 5,340,360 A | 8/1994 | Stefanchik |
| 5,342,393 A | 8/1994 | Stack |
| 5,350,399 A | 9/1994 | Erlebacher et al. |
| 5,352,229 A | 10/1994 | Goble et al. |
| 5,364,406 A | 11/1994 | Sewell, Jr. |
| 5,364,408 A | 11/1994 | Gordon |
| 5,366,458 A | 11/1994 | Korthoff et al. |
| 5,366,479 A | 11/1994 | McGarry et al. |
| 5,383,896 A | 1/1995 | Gershony et al. |
| RE34,866 E | 2/1995 | Kensey et al. |
| 5,392,978 A | 2/1995 | Valez et al. |
| 5,395,030 A | 3/1995 | Kuramoto et al. |
| 5,411,520 A | 5/1995 | Nash et al. |
| 5,413,571 A | 5/1995 | Katsaros et al. |
| 5,413,584 A | 5/1995 | Schulze |
| 5,416,584 A | 5/1995 | Kay |
| 5,417,699 A | 5/1995 | Klein et al. |
| 5,419,777 A | 5/1995 | Hofling |
| 5,423,857 A | 6/1995 | Rosenman et al. |
| 5,425,489 A | 6/1995 | Shichman et al. |
| 5,425,740 A | 6/1995 | Hutchinson, Jr. |
| 5,431,639 A | 7/1995 | Shaw |
| 5,431,667 A | 7/1995 | Thompson et al. |
| 5,433,721 A | 7/1995 | Hooven et al. |
| 5,437,631 A | 8/1995 | Janzen |
| 5,439,479 A | 8/1995 | Shichman et al. |
| 5,443,477 A | 8/1995 | Marin et al. |
| 5,443,481 A | 8/1995 | Lee |
| 5,445,167 A | 8/1995 | Yoon et al. |
| 5,449,359 A | 9/1995 | Groiso |
| 5,456,400 A | 10/1995 | Shichman et al. |
| 5,462,561 A | 10/1995 | Voda |
| 5,464,413 A | 11/1995 | Siska, Jr. et al. |
| 5,466,241 A | 11/1995 | Leroy et al. |
| 5,470,010 A | 11/1995 | Rothfuss et al. |
| 5,474,557 A | 12/1995 | Mai |
| 5,474,569 A | 12/1995 | Zinreich et al. |
| 5,476,505 A | 12/1995 | Limon |
| 5,478,352 A | 12/1995 | Fowler |
| 5,478,353 A | 12/1995 | Yoon |
| 5,478,354 A | 12/1995 | Tovey et al. |
| 5,486,195 A | 1/1996 | Myers et al. |
| 5,497,933 A | 3/1996 | DeFonzo et al. |
| 5,507,744 A | 4/1996 | Tay et al. |
| 5,507,755 A | 4/1996 | Gresl et al. |
| 5,522,840 A | 6/1996 | Krajicek |
| 5,527,322 A | 6/1996 | Klein et al. |
| 5,536,251 A | 7/1996 | Evard et al. |
| 5,540,712 A | 7/1996 | Kleshinski et al. |
| 5,540,716 A | 7/1996 | Hlavacek |
| 5,544,802 A | 8/1996 | Crainich |
| 5,547,474 A | 8/1996 | Kloeckl et al. |
| 5,560,532 A | 10/1996 | DeFonzo et al. |
| 5,571,120 A | 11/1996 | Yoon |
| 5,573,784 A | 11/1996 | Badylak et al. |
| 5,575,771 A | 11/1996 | Walinsky |
| 5,584,879 A | 12/1996 | Reimold et al. |
| 5,591,205 A | 1/1997 | Fowler |
| 5,593,412 A | 1/1997 | Martinez et al. |
| 5,601,602 A | 2/1997 | Fowler |
| 5,609,597 A | 3/1997 | Lehrer |
| 5,613,974 A | 3/1997 | Andreas et al. |
| 5,618,291 A | 4/1997 | Thompson et al. |
| 5,620,452 A | 4/1997 | Yoon |
| 5,620,461 A | 4/1997 | Muijs et al. |
| 5,643,318 A | 7/1997 | Tsukernik et al. |
| 5,645,565 A | 7/1997 | Rudd et al. |
| 5,645,566 A | 7/1997 | Brenneman et al. |
| 5,645,567 A | 7/1997 | Crainich |
| 5,649,959 A | 7/1997 | Hannam et al. |
| D383,539 S | 9/1997 | Croley |
| 5,674,231 A | 10/1997 | Green et al. |
| 5,676,689 A | 10/1997 | Kensey et al. |
| 5,676,974 A | 10/1997 | Valdes et al. |
| 5,681,334 A | 10/1997 | Evans et al. |
| 5,683,405 A | 11/1997 | Yacoubian et al. |
| 5,690,674 A | 11/1997 | Diaz |
| 5,695,504 A | 12/1997 | Gifford, III et al. |
| 5,695,505 A | 12/1997 | Yoon |
| 5,695,524 A | 12/1997 | Kelley et al. |
| 5,700,273 A | 12/1997 | Buelna et al. |
| 5,716,375 A | 2/1998 | Fowler |
| 5,720,755 A | 2/1998 | Dakov |
| 5,725,498 A | 3/1998 | Janzen et al. |
| 5,725,552 A | 3/1998 | Kotula et al. |
| 5,725,554 A | 3/1998 | Simon et al. |
| 5,728,110 A | 3/1998 | Vidal et al. |
| 5,728,114 A | 3/1998 | Evans et al. |
| 5,728,122 A | 3/1998 | Leschinsky et al. |
| 5,728,132 A | 3/1998 | Van Tassel et al. |
| 5,728,133 A | 3/1998 | Kontos |
| 5,732,872 A | 3/1998 | Bolduc et al. |
| 5,735,873 A | 4/1998 | MacLean |
| 5,752,966 A | 5/1998 | Chang |
| 5,755,726 A | 5/1998 | Pratt et al. |
| 5,755,778 A | 5/1998 | Kleshinski |
| 5,766,217 A | 6/1998 | Christy |
| 5,766,246 A | 6/1998 | Mulhauser et al. |
| 5,769,870 A | 6/1998 | Salahieh et al. |
| 5,776,147 A | 7/1998 | Dolendo |
| 5,779,707 A | 7/1998 | Bertholet et al. |
| 5,782,844 A | 7/1998 | Yoon et al. |
| 5,782,860 A | 7/1998 | Epstein et al. |
| 5,782,861 A | 7/1998 | Cragg et al. |
| 5,795,958 A | 8/1998 | Rao et al. |
| 5,797,928 A | 8/1998 | Kogasaka |
| 5,797,931 A | 8/1998 | Bito et al. |
| 5,797,933 A | 8/1998 | Snow et al. |
| 5,797,958 A | 8/1998 | Yoon |
| 5,810,776 A | 9/1998 | Bacich et al. |
| 5,810,846 A | 9/1998 | Virnich et al. |
| 5,810,851 A | 9/1998 | Yoon |
| 5,817,113 A | 10/1998 | Gifford, III et al. |
| 5,820,631 A | 10/1998 | Nobles |
| 5,827,298 A | 10/1998 | Hart et al. |
| 5,830,125 A | 11/1998 | Scribner et al. |
| 5,833,698 A | 11/1998 | Hinchliffe et al. |
| 5,843,167 A | 12/1998 | Dwyer et al. |
| 5,853,421 A | 12/1998 | Leschinsky et al. |
| 5,853,422 A | 12/1998 | Huebsch et al. |
| 5,855,312 A | 1/1999 | Toledano |
| 5,858,082 A | 1/1999 | Cruz et al. |
| 5,860,991 A | 1/1999 | Klein et al. |
| 5,861,005 A | 1/1999 | Kontos |
| 5,868,755 A | 2/1999 | Kanner et al. |

| Patent | | Date | Inventor |
|---|---|---|---|
| 5,868,763 | A * | 2/1999 | Spence et al. .............. 606/153 |
| 5,871,474 | A | 2/1999 | Hermann et al. |
| 5,871,501 | A | 2/1999 | Leschinsky et al. |
| 5,871,525 | A | 2/1999 | Edwards et al. |
| 5,873,876 | A | 2/1999 | Christy |
| 5,879,366 | A | 3/1999 | Shaw et al. |
| 5,891,088 | A | 4/1999 | Thompson et al. |
| 5,897,487 | A | 4/1999 | Ouchi |
| 5,902,310 | A | 5/1999 | Foerster et al. |
| 5,904,697 | A | 5/1999 | Gifford, III et al. |
| 5,906,631 | A | 5/1999 | Imran |
| 5,907,893 | A * | 6/1999 | Zadno-Azizi et al. .......... 29/6.1 |
| 5,910,155 | A | 6/1999 | Ratcliff et al. |
| 5,919,207 | A | 7/1999 | Taheri |
| 5,922,009 | A | 7/1999 | Epstein et al. |
| 5,928,231 | A | 7/1999 | Klein et al. |
| 5,928,251 | A | 7/1999 | Aranyi et al. |
| 5,935,147 | A | 8/1999 | Kensey et al. |
| 5,938,667 | A | 8/1999 | Peyser et al. |
| 5,941,890 | A | 8/1999 | Voegele et al. |
| 5,947,999 | A | 9/1999 | Groiso |
| 5,951,518 | A | 9/1999 | Licata et al. |
| 5,951,576 | A | 9/1999 | Wakabayashi |
| 5,951,589 | A | 9/1999 | Epstein et al. |
| 5,957,936 | A | 9/1999 | Yoon et al. |
| 5,957,938 | A | 9/1999 | Zhu et al. |
| 5,957,940 | A | 9/1999 | Tanner et al. |
| 5,964,782 | A | 10/1999 | Lafontaine et al. |
| 5,976,161 | A | 11/1999 | Kirsch et al. |
| 5,984,934 | A | 11/1999 | Ashby et al. |
| 5,984,949 | A | 11/1999 | Levin |
| 5,993,468 | A | 11/1999 | Rygaard |
| 5,993,476 | A | 11/1999 | Groiso |
| 6,001,110 | A | 12/1999 | Adams |
| 6,004,341 | A | 12/1999 | Zhu et al. |
| 6,007,563 | A | 12/1999 | Nash et al. |
| 6,010,517 | A | 1/2000 | Baccaro |
| 6,013,084 | A | 1/2000 | Ken et al. |
| 6,015,815 | A | 1/2000 | Mollison |
| 6,019,779 | A | 2/2000 | Thorud et al. |
| 6,022,372 | A | 2/2000 | Kontos |
| 6,024,750 | A | 2/2000 | Mastri |
| 6,030,364 | A | 2/2000 | Durgin et al. |
| 6,030,413 | A | 2/2000 | Lazarus |
| 6,033,427 | A | 3/2000 | Lee |
| 6,036,703 | A | 3/2000 | Evans et al. |
| 6,036,720 | A | 3/2000 | Abrams et al. |
| 6,045,570 | A | 4/2000 | Epstein et al. |
| 6,048,358 | A | 4/2000 | Barak |
| 6,056,768 | A | 5/2000 | Cates et al. |
| 6,056,769 | A | 5/2000 | Epstein et al. |
| 6,056,770 | A | 5/2000 | Epstein et al. |
| 6,059,800 | A | 5/2000 | Hart et al. |
| 6,059,825 | A | 5/2000 | Hobbs et al. |
| 6,063,085 | A | 5/2000 | Tay et al. |
| 6,063,114 | A | 5/2000 | Nash et al. |
| 6,071,300 | A | 6/2000 | Brenneman et al. |
| 6,077,281 | A | 6/2000 | Das |
| 6,077,291 | A | 6/2000 | Das |
| 6,080,182 | A | 6/2000 | Shaw et al. |
| 6,080,183 | A | 6/2000 | Tsugita et al. |
| 6,090,130 | A | 7/2000 | Nash et al. |
| 6,102,271 | A | 8/2000 | Longo et al. |
| 6,110,184 | A | 8/2000 | Weadock |
| 6,113,612 | A | 9/2000 | Swanson et al. |
| 6,117,125 | A | 9/2000 | Rothbarth et al. |
| 6,117,148 | A | 9/2000 | Ravo |
| 6,117,157 | A | 9/2000 | Tekulve |
| 6,120,524 | A | 9/2000 | Taheri |
| 6,126,675 | A | 10/2000 | Schervinsky et al. |
| 6,136,010 | A | 10/2000 | Modesitt et al. |
| 6,149,660 | A | 11/2000 | Laufer et al. |
| 6,149,667 | A | 11/2000 | Hovland et al. |
| 6,152,144 | A | 11/2000 | Lesh et al. |
| 6,152,936 | A | 11/2000 | Christy et al. |
| 6,152,937 | A | 11/2000 | Peterson et al. |
| 6,165,204 | A | 12/2000 | Levinson et al. |
| 6,171,277 | B1 | 1/2001 | Ponzi |
| 6,171,329 | B1 | 1/2001 | Shaw et al. |
| 6,179,849 | B1 | 1/2001 | Yencho et al. |
| 6,193,708 | B1 | 2/2001 | Ken et al. |
| 6,193,734 | B1 | 2/2001 | Bolduc et al. |
| 6,197,042 | B1 | 3/2001 | Ginn et al. |
| 6,198,974 | B1 | 3/2001 | Webster, Jr. |
| 6,200,329 | B1 | 3/2001 | Fung et al. |
| 6,206,895 | B1 | 3/2001 | Levinson |
| 6,206,913 | B1 | 3/2001 | Yencho et al. |
| 6,206,931 | B1 | 3/2001 | Cook et al. |
| 6,210,407 | B1 | 4/2001 | Webster |
| 6,220,248 | B1 | 4/2001 | Voegele et al. |
| 6,221,102 | B1 | 4/2001 | Baker et al. |
| 6,245,079 | B1 | 6/2001 | Nobles et al. |
| 6,248,124 | B1 | 6/2001 | Pedros et al. |
| 6,254,617 | B1 | 7/2001 | Spence et al. |
| 6,254,642 | B1 | 7/2001 | Taylor |
| 6,267,773 | B1 | 7/2001 | Gadberry et al. |
| 6,273,903 | B1 | 8/2001 | Wilk |
| 6,277,140 | B2 | 8/2001 | Ginn et al. |
| 6,280,460 | B1 | 8/2001 | Bolduc et al. |
| 6,287,322 | B1 | 9/2001 | Zhu et al. |
| 6,296,657 | B1 | 10/2001 | Brucker |
| 6,305,891 | B1 | 10/2001 | Burlingame |
| 6,319,258 | B1 | 11/2001 | McAllen, III et al. |
| 6,322,580 | B1 | 11/2001 | Kanner |
| 6,328,727 | B1 | 12/2001 | Frazier et al. |
| 6,329,386 | B1 | 12/2001 | Mollison |
| 6,334,865 | B1 | 1/2002 | Redmond et al. |
| 6,348,064 | B1 | 2/2002 | Kanner |
| 6,358,258 | B1 | 3/2002 | Arcia et al. |
| 6,375,671 | B1 | 4/2002 | Kobayashi et al. |
| D457,958 | S | 5/2002 | Dycus |
| 6,383,208 | B1 | 5/2002 | Sancoff et al. |
| 6,391,048 | B1 | 5/2002 | Ginn et al. |
| 6,395,015 | B1 | 5/2002 | Borst et al. |
| 6,398,752 | B1 | 6/2002 | Sweezer et al. |
| 6,402,765 | B1 | 6/2002 | Monassevitch et al. |
| 6,409,739 | B1 | 6/2002 | Nobles et al. |
| 6,419,669 | B1 | 7/2002 | Frazier et al. |
| 6,423,054 | B1 | 7/2002 | Ouchi |
| 6,425,911 | B1 | 7/2002 | Akerfeldt et al. |
| 6,428,472 | B1 | 8/2002 | Haas |
| 6,428,548 | B1 | 8/2002 | Durgin et al. |
| 6,443,158 | B1 | 9/2002 | Lafontaine et al. |
| 6,443,963 | B1 | 9/2002 | Baldwin et al. |
| 6,447,540 | B1 | 9/2002 | Fontaine et al. |
| 6,450,391 | B1 | 9/2002 | Kayan et al. |
| 6,458,130 | B1 | 10/2002 | Frazier et al. |
| 6,461,364 | B1 | 10/2002 | Ginn et al. |
| 6,482,224 | B1 | 11/2002 | Michler et al. |
| 6,488,692 | B1 | 12/2002 | Spence et al. |
| 6,500,115 | B2 | 12/2002 | Krattiger et al. |
| 6,506,210 | B1 | 1/2003 | Kanner |
| 6,508,828 | B1 | 1/2003 | Akerfeldt et al. |
| 6,517,569 | B2 | 2/2003 | Mikus et al. |
| 6,533,762 | B2 | 3/2003 | Kanner et al. |
| 6,533,812 | B2 | 3/2003 | Swanson et al. |
| 6,537,288 | B2 | 3/2003 | Vargas et al. |
| 6,547,806 | B1 | 4/2003 | Ding |
| 6,551,319 | B2 | 4/2003 | Lieberman |
| 6,569,173 | B1 | 5/2003 | Blatter et al. |
| 6,569,185 | B2 | 5/2003 | Ungs |
| 6,572,629 | B2 | 6/2003 | Kalloo et al. |
| 6,582,452 | B2 | 6/2003 | Coleman et al. |
| 6,582,482 | B2 | 6/2003 | Gillman et al. |
| 6,596,012 | B2 | 7/2003 | Akerfeldt et al. |
| 6,599,303 | B1 | 7/2003 | Peterson et al. |
| 6,602,263 | B1 | 8/2003 | Swanson et al. |
| 6,610,072 | B1 | 8/2003 | Christy et al. |
| 6,613,059 | B2 | 9/2003 | Schaller et al. |
| 6,616,686 | B2 | 9/2003 | Coleman et al. |
| 6,623,509 | B2 | 9/2003 | Ginn |
| 6,623,510 | B2 | 9/2003 | Carley et al. |
| 6,626,918 | B1 | 9/2003 | Ginn et al. |
| 6,626,920 | B2 | 9/2003 | Whayne |
| 6,632,238 | B2 | 10/2003 | Ginn et al. |
| 6,634,537 | B2 | 10/2003 | Chen |
| 6,645,205 | B2 | 11/2003 | Ginn |
| 6,652,538 | B2 | 11/2003 | Kayan et al. |

| | | |
|---|---|---|
| 6,652,556 B1 | 11/2003 | VanTassel et al. |
| 6,663,655 B2 | 12/2003 | Ginn et al. |
| 6,669,714 B2 | 12/2003 | Coleman et al. |
| 6,673,083 B1 | 1/2004 | Kayan et al. |
| 6,676,671 B2 | 1/2004 | Robertson et al. |
| 6,676,685 B2 | 1/2004 | Pedros et al. |
| 6,679,904 B2 | 1/2004 | Gleeson et al. |
| 6,689,147 B1 | 2/2004 | Koster, Jr. |
| 6,695,867 B2 | 2/2004 | Ginn et al. |
| 6,699,256 B1 | 3/2004 | Logan et al. |
| 6,702,826 B2 | 3/2004 | Liddicoat et al. |
| 6,712,836 B1 | 3/2004 | Berg et al. |
| 6,712,837 B2 | 3/2004 | Akerfeldt et al. |
| 6,719,777 B2 | 4/2004 | Ginn et al. |
| 6,726,704 B1 | 4/2004 | Loshakove et al. |
| 6,743,195 B2 | 6/2004 | Zucker |
| 6,743,243 B1 | 6/2004 | Roy et al. |
| 6,743,259 B2 | 6/2004 | Ginn |
| 6,749,621 B2 | 6/2004 | Pantages et al. |
| 6,749,622 B2 | 6/2004 | McGuckin et al. |
| 6,755,842 B2 | 6/2004 | Kanner et al. |
| 6,767,356 B2 | 7/2004 | Kanner et al. |
| 6,780,197 B2 | 8/2004 | Roe et al. |
| 6,786,915 B2 | 9/2004 | Akerfeldt et al. |
| 6,790,218 B2 | 9/2004 | Jayaraman |
| 6,790,220 B2 | 9/2004 | Morris et al. |
| 6,837,906 B2 | 1/2005 | Ginn |
| 6,846,319 B2 | 1/2005 | Ginn et al. |
| 6,860,895 B1 | 3/2005 | Akerfeldt et al. |
| 6,890,343 B2 | 5/2005 | Ginn et al. |
| 6,896,687 B2 | 5/2005 | Dakov |
| 6,896,692 B2 | 5/2005 | Ginn et al. |
| 6,926,723 B1 | 8/2005 | Mulhauser et al. |
| 6,926,731 B2 | 8/2005 | Coleman et al. |
| 6,929,634 B2 | 8/2005 | Dorros et al. |
| 6,942,674 B2 | 9/2005 | Belef et al. |
| 6,942,691 B1 | 9/2005 | Chuter |
| 6,964,668 B2 | 11/2005 | Modesitt et al. |
| 6,969,397 B2 | 11/2005 | Ginn |
| 6,989,003 B2 | 1/2006 | Wing et al. |
| 6,989,016 B2 | 1/2006 | Tallarida et al. |
| 7,001,398 B2 | 2/2006 | Carley et al. |
| 7,001,400 B1 | 2/2006 | Modesitt et al. |
| 7,008,435 B2 | 3/2006 | Cummins |
| 7,008,439 B1 | 3/2006 | Janzen et al. |
| 7,033,379 B2 | 4/2006 | Peterson |
| 7,060,084 B1 | 6/2006 | Loshakove et al. |
| 7,063,711 B1 | 6/2006 | Loshakove et al. |
| 7,083,635 B2 | 8/2006 | Ginn |
| 7,108,709 B2 | 9/2006 | Cummins |
| 7,111,768 B2 | 9/2006 | Cummins et al. |
| 7,112,225 B2 | 9/2006 | Ginn |
| 7,144,411 B2 | 12/2006 | Ginn et al. |
| 7,163,551 B2 | 1/2007 | Anthony et al. |
| 7,169,158 B2 | 1/2007 | Sniffin et al. |
| 7,169,164 B2 | 1/2007 | Borillo et al. |
| 7,211,101 B2 | 5/2007 | Carley et al. |
| 7,261,716 B2 | 8/2007 | Strobel et al. |
| 7,311,720 B2 | 12/2007 | Mueller et al. |
| 7,316,704 B2 | 1/2008 | Bagaoisan et al. |
| 7,322,995 B2 | 1/2008 | Buckman et al. |
| 7,326,230 B2 | 2/2008 | Ravikumar |
| 7,331,979 B2 | 2/2008 | Khosravi et al. |
| 7,335,220 B2 | 2/2008 | Khosravi et al. |
| D566,272 S | 4/2008 | Walberg et al. |
| 7,361,178 B2 | 4/2008 | Hearn et al. |
| 7,361,183 B2 | 4/2008 | Ginn |
| 7,361,185 B2 | 4/2008 | O'Malley et al. |
| 7,393,363 B2 | 7/2008 | Ginn |
| 7,396,359 B1 | 7/2008 | Derowe et al. |
| 7,533,790 B1 | 5/2009 | Knodel et al. |
| 7,582,103 B2 | 9/2009 | Young et al. |
| 7,597,706 B2 | 10/2009 | Kanner et al. |
| D611,144 S | 3/2010 | Reynolds |
| 7,806,904 B2 * | 10/2010 | Carley et al. .................. 606/151 |
| 7,819,895 B2 | 10/2010 | Ginn et al. |
| 7,841,502 B2 | 11/2010 | Walberg et al. |
| 7,842,068 B2 | 11/2010 | Ginn |
| 7,850,709 B2 | 12/2010 | Cummins et al. |
| 7,850,797 B2 | 12/2010 | Carley et al. |
| 7,854,810 B2 | 12/2010 | Carley et al. |
| 7,857,828 B2 | 12/2010 | Jabba et al. |
| 7,867,249 B2 | 1/2011 | Palermo et al. |
| 7,879,071 B2 * | 2/2011 | Carley et al. .................. 606/158 |
| 7,931,671 B2 | 4/2011 | Tenerz |
| 8,105,352 B2 | 1/2012 | Egnelov |
| 2001/0007077 A1 | 7/2001 | Ginn et al. |
| 2001/0031972 A1 | 10/2001 | Robertson et al. |
| 2001/0046518 A1 | 11/2001 | Sawhney |
| 2001/0047180 A1 | 11/2001 | Grudem et al. |
| 2002/0026215 A1 | 2/2002 | Redmond et al. |
| 2002/0038127 A1 | 3/2002 | Blatter et al. |
| 2002/0042622 A1 | 4/2002 | Vargas et al. |
| 2002/0049427 A1 | 4/2002 | Wiener et al. |
| 2002/0058960 A1 | 5/2002 | Hudson et al. |
| 2002/0077657 A1 | 6/2002 | Ginn et al. |
| 2002/0082641 A1 | 6/2002 | Ginn et al. |
| 2002/0099389 A1 | 7/2002 | Michler et al. |
| 2002/0106409 A1 | 8/2002 | Sawhney et al. |
| 2002/0107542 A1 | 8/2002 | Kanner et al. |
| 2002/0133193 A1 | 9/2002 | Ginn et al. |
| 2002/0151921 A1 | 10/2002 | Kanner et al. |
| 2002/0183786 A1 | 12/2002 | Girton |
| 2002/0183787 A1 | 12/2002 | Wahr et al. |
| 2002/0198589 A1 | 12/2002 | Leong |
| 2003/0004543 A1 | 1/2003 | Gleeson et al. |
| 2003/0009180 A1 | 1/2003 | Hinchliffe et al. |
| 2003/0032981 A1 | 2/2003 | Kanner et al. |
| 2003/0045893 A1 | 3/2003 | Ginn |
| 2003/0055455 A1 | 3/2003 | Yang et al. |
| 2003/0065358 A1 | 4/2003 | Frecker et al. |
| 2003/0078598 A1 | 4/2003 | Ginn et al. |
| 2003/0083679 A1 | 5/2003 | Grudem et al. |
| 2003/0093096 A1 | 5/2003 | McGuckin et al. |
| 2003/0097140 A1 | 5/2003 | Kanner |
| 2003/0109890 A1 | 6/2003 | Kanner et al. |
| 2003/0125766 A1 | 7/2003 | Ding |
| 2003/0144695 A1 | 7/2003 | McGuckin, Jr. et al. |
| 2003/0158577 A1 | 8/2003 | Pantages et al. |
| 2003/0158578 A1 | 8/2003 | Pantages et al. |
| 2003/0195504 A1 | 10/2003 | Tallarida et al. |
| 2003/0195561 A1 | 10/2003 | Carley et al. |
| 2004/0009205 A1 | 1/2004 | Sawhney |
| 2004/0009289 A1 | 1/2004 | Carley et al. |
| 2004/0059376 A1 | 3/2004 | Breuniger |
| 2004/0068273 A1 | 4/2004 | Fariss et al. |
| 2004/0073236 A1 | 4/2004 | Carley et al. |
| 2004/0073255 A1 | 4/2004 | Ginn et al. |
| 2004/0082906 A1 | 4/2004 | Tallarida et al. |
| 2004/0087985 A1 | 5/2004 | Loshakove et al. |
| 2004/0092964 A1 | 5/2004 | Modesitt et al. |
| 2004/0092968 A1 | 5/2004 | Caro et al. |
| 2004/0093024 A1 | 5/2004 | Lousararian et al. |
| 2004/0093027 A1 | 5/2004 | Fabisiak et al. |
| 2004/0097978 A1 | 5/2004 | Modesitt et al. |
| 2004/0127940 A1 | 7/2004 | Ginn et al. |
| 2004/0143290 A1 | 7/2004 | Brightbill |
| 2004/0153122 A1 | 8/2004 | Palermo |
| 2004/0158127 A1 | 8/2004 | Okada |
| 2004/0158287 A1 | 8/2004 | Cragg et al. |
| 2004/0158309 A1 | 8/2004 | Wachter et al. |
| 2004/0167511 A1 | 8/2004 | Buehlmann et al. |
| 2004/0167570 A1 | 8/2004 | Pantages |
| 2004/0191277 A1 | 9/2004 | Sawhney et al. |
| 2004/0215232 A1 | 10/2004 | Belhe et al. |
| 2004/0249412 A1 | 12/2004 | Snow et al. |
| 2004/0254591 A1 | 12/2004 | Kanner et al. |
| 2004/0267193 A1 | 12/2004 | Bagaoisan et al. |
| 2004/0267308 A1 | 12/2004 | Bagaoisan et al. |
| 2004/0267312 A1 | 12/2004 | Kanner et al. |
| 2005/0038460 A1 | 2/2005 | Jayaraman |
| 2005/0038500 A1 | 2/2005 | Boylan et al. |
| 2005/0059982 A1 | 3/2005 | Zung et al. |
| 2005/0075665 A1 | 4/2005 | Brenzel et al. |
| 2005/0085851 A1 | 4/2005 | Fiehler et al. |
| 2005/0085854 A1 | 4/2005 | Ginn |
| 2005/0085855 A1 | 4/2005 | Forsberg |
| 2005/0090859 A1 | 4/2005 | Ravlkumar |

| | | |
|---|---|---|
| 2005/0119695 A1 | 6/2005 | Carley et al. |
| 2005/0121042 A1 | 6/2005 | Belhe et al. |
| 2005/0149117 A1 | 7/2005 | Khosravi et al. |
| 2005/0152949 A1 | 7/2005 | Hotchkiss et al. |
| 2005/0165357 A1 | 7/2005 | McGuckin et al. |
| 2005/0169974 A1 | 8/2005 | Tenerz et al. |
| 2005/0177189 A1 | 8/2005 | Ginn et al. |
| 2005/0187564 A1 | 8/2005 | Jayaraman |
| 2005/0216057 A1 | 9/2005 | Coleman et al. |
| 2005/0222614 A1 | 10/2005 | Ginn et al. |
| 2005/0245876 A1 | 11/2005 | Khosravi et al. |
| 2005/0267528 A1 | 12/2005 | Ginn et al. |
| 2005/0267530 A1 | 12/2005 | Cummins et al. |
| 2005/0273136 A1 | 12/2005 | Belef et al. |
| 2005/0273137 A1 | 12/2005 | Ginn |
| 2005/0274768 A1 | 12/2005 | Cummins et al. |
| 2005/0283188 A1 | 12/2005 | Loshakove et al. |
| 2006/0030867 A1 | 2/2006 | Zadno |
| 2006/0034930 A1 | 2/2006 | Khosravi et al. |
| 2006/0047313 A1 | 3/2006 | Khanna et al. |
| 2006/0100664 A1 | 5/2006 | Pai et al. |
| 2006/0167484 A1 | 7/2006 | Carley et al. |
| 2006/0190014 A1 | 8/2006 | Ginn et al. |
| 2006/0190037 A1 | 8/2006 | Ginn et al. |
| 2006/0190038 A1 | 8/2006 | Carley et al. |
| 2006/0195123 A1 | 8/2006 | Ginn et al. |
| 2006/0195124 A1 | 8/2006 | Ginn et al. |
| 2006/0206146 A1 | 9/2006 | Tenerz |
| 2006/0253037 A1 | 11/2006 | Ginn et al. |
| 2006/0253072 A1 | 11/2006 | Pai et al. |
| 2006/0287674 A1 | 12/2006 | Ginn et al. |
| 2006/0293698 A1 | 12/2006 | Douk |
| 2007/0010853 A1 | 1/2007 | Ginn et al. |
| 2007/0010854 A1 | 1/2007 | Cummins et al. |
| 2007/0021778 A1 | 1/2007 | Carly |
| 2007/0060950 A1 | 3/2007 | Khosravi et al. |
| 2007/0083230 A1 | 4/2007 | Javois |
| 2007/0112304 A1 | 5/2007 | Voss |
| 2007/0112365 A1 | 5/2007 | Hilal et al. |
| 2007/0123816 A1 | 5/2007 | Zhu et al. |
| 2007/0123817 A1 | 5/2007 | Khosravi et al. |
| 2007/0179527 A1 | 8/2007 | Eskuri et al. |
| 2007/0203507 A1 | 8/2007 | McLaughlin et al. |
| 2007/0225755 A1 | 9/2007 | Preinitz et al. |
| 2007/0225756 A1 | 9/2007 | Preinitz et al. |
| 2007/0225757 A1 | 9/2007 | Preinitz et al. |
| 2007/0225758 A1 | 9/2007 | Preinitz et al. |
| 2007/0239209 A1 | 10/2007 | Fallman |
| 2007/0250080 A1 | 10/2007 | Jones et al. |
| 2007/0265658 A1 | 11/2007 | Nelson et al. |
| 2007/0270904 A1 | 11/2007 | Ginn |
| 2007/0276416 A1 | 11/2007 | Ginn et al. |
| 2007/0276488 A1 | 11/2007 | Wachter et al. |
| 2007/0282352 A1 | 12/2007 | Carley et al. |
| 2008/0004636 A1 | 1/2008 | Walberg et al. |
| 2008/0004640 A1 | 1/2008 | Ellingwood |
| 2008/0009794 A1 | 1/2008 | Bagaoisan et al. |
| 2008/0058839 A1 | 3/2008 | Nobles et al. |
| 2008/0065151 A1 | 3/2008 | Ginn |
| 2008/0065152 A1 | 3/2008 | Carley |
| 2008/0086075 A1 | 4/2008 | Isik et al. |
| 2008/0093414 A1 | 4/2008 | Bender et al. |
| 2008/0114395 A1 | 5/2008 | Mathisen et al. |
| 2008/0210737 A1 | 9/2008 | Ginn et al. |
| 2008/0221616 A1 | 9/2008 | Ginn et al. |
| 2008/0243148 A1 | 10/2008 | Mikkaichi et al. |
| 2008/0269801 A1 | 10/2008 | Coleman et al. |
| 2008/0269802 A1 | 10/2008 | Coleman et al. |
| 2008/0272173 A1 | 11/2008 | Coleman et al. |
| 2008/0300628 A1 | 12/2008 | Ellingwood |
| 2008/0312666 A1 | 12/2008 | Ellingwood et al. |
| 2008/0312686 A1 | 12/2008 | Ellingwood |
| 2008/0312740 A1 | 12/2008 | Wachter et al. |
| 2008/0319475 A1 | 12/2008 | Clark |
| 2009/0112306 A1 | 4/2009 | Bonsignore et al. |
| 2009/0137900 A1 | 5/2009 | Bonner et al. |
| 2009/0157101 A1 | 6/2009 | Reyes et al. |
| 2009/0157102 A1 | 6/2009 | Reynolds et al. |
| 2009/0177212 A1 | 7/2009 | Carley et al. |
| 2009/0187215 A1 | 7/2009 | Mackiewicz et al. |
| 2009/0216267 A1 | 8/2009 | Willard et al. |
| 2009/0230168 A1 | 9/2009 | Coleman et al. |
| 2009/0287244 A1 | 11/2009 | Kokish |
| 2009/0312789 A1 | 12/2009 | Kassab et al. |
| 2010/0114156 A1 | 5/2010 | Mehl |
| 2010/0114159 A1 | 5/2010 | Roorda et al. |
| 2010/0160958 A1 | 6/2010 | Clark |
| 2010/0168790 A1 | 7/2010 | Clark |
| 2010/0179567 A1 | 7/2010 | Voss et al. |
| 2010/0179571 A1 | 7/2010 | Voss |
| 2010/0179572 A1 | 7/2010 | Voss et al. |
| 2010/0179589 A1 | 7/2010 | Roorda et al. |
| 2010/0179590 A1 | 7/2010 | Fortson et al. |
| 2010/0185234 A1 | 7/2010 | Fortson et al. |
| 2010/0217132 A1 | 8/2010 | Ellingwood et al. |
| 2011/0178548 A1 | 7/2011 | Tenerz |

FOREIGN PATENT DOCUMENTS

| | | |
|---|---|---|
| CA | 2 339 060 | 2/2000 |
| DE | 197 11 288 | 10/1998 |
| DE | 29723736 U1 | 4/1999 |
| DE | 19859952 | 2/2000 |
| DE | 102006056283 | 6/2008 |
| EP | 0 386 361 | 9/1990 |
| EP | 0 534 696 | 3/1993 |
| EP | 0 756 851 | 2/1997 |
| EP | 0 774 237 | 5/1997 |
| EP | 0 858 776 | 8/1998 |
| EP | 0 941 697 | 9/1999 |
| EP | 1 867 287 | 12/2007 |
| FR | 2 443 238 | 7/1980 |
| FR | 2 715 290 | 7/1995 |
| FR | 2 722 975 | 2/1996 |
| FR | 2 768 324 | 3/1999 |
| GB | 1 358 466 | 7/1974 |
| GB | 2 075 144 | 11/1981 |
| GB | 2 397 240 | 7/2004 |
| IE | S2000/0722 | 10/2001 |
| IE | S2000/0724 | 10/2001 |
| IE | S2001/0547 | 7/2002 |
| IE | S2001/0815 | 7/2002 |
| IE | S2001/0748 | 8/2002 |
| IE | S2001/0749 | 8/2002 |
| IE | S2002/0452 | 12/2002 |
| IE | S2002/0664 | 2/2003 |
| IE | S2002/0665 | 2/2003 |
| IE | S2002/0451 | 7/2003 |
| IE | S2002/0552 | 7/2003 |
| IE | S2003/0424 | 12/2003 |
| IE | S2003/0490 | 1/2004 |
| IE | S2004/0368 | 11/2005 |
| IE | S2005/0342 | 11/2005 |
| JP | 58-181006 | 12/1983 |
| JP | 12 74750 | 11/1989 |
| JP | 2000102546 | 4/2000 |
| NL | 9302140 | 7/1995 |
| PL | 171425 | 4/1997 |
| RU | 2086192 | 8/1997 |
| SU | 495067 | 12/1975 |
| SU | 912155 | 3/1982 |
| SU | 1243708 | 7/1986 |
| SU | 1324650 | 7/1987 |
| SU | 1405828 | 6/1988 |
| SU | 1456109 | 2/1989 |
| SU | 1560133 | 4/1990 |
| WO | WO 96/24291 | 8/1996 |
| WO | WO 97/07741 | 3/1997 |
| WO | WO 97/20505 | 6/1997 |
| WO | WO 97/27897 | 8/1997 |
| WO | WO 98/06346 | 2/1998 |
| WO | WO 98/06448 | 2/1998 |
| WO | WO 98/16161 | 4/1998 |
| WO | WO 98/17179 | 4/1998 |
| WO | WO 98/18389 | 5/1998 |
| WO | WO 98/24374 | 6/1998 |
| WO | WO 98/25508 | 6/1998 |
| WO | WO 98/58591 | 12/1998 |
| WO | WO 99/21491 | 5/1999 |

| | | |
|---|---|---|
| WO | WO 99/40849 | 8/1999 |
| WO | WO 99/60941 | 12/1999 |
| WO | WO 99/62408 | 12/1999 |
| WO | WO 99/62415 | 12/1999 |
| WO | WO 00/06029 | 2/2000 |
| WO | WO 00/07505 | 2/2000 |
| WO | WO 00/07640 | 2/2000 |
| WO | WO 00/27311 | 5/2000 |
| WO | WO 00/27313 | 5/2000 |
| WO | WO 00/56223 * | 9/2000 |
| WO | WO 00/56227 | 9/2000 |
| WO | WO 00/56228 | 9/2000 |
| WO | WO 00/71032 | 11/2000 |
| WO | WO 01/21058 | 3/2001 |
| WO | WO 01/35832 | 5/2001 |
| WO | WO 01/47594 | 7/2001 |
| WO | WO 01/49186 | 7/2001 |
| WO | WO 01/91628 | 12/2001 |
| WO | WO 02/19915 | 3/2002 |
| WO | WO 02/19920 | 3/2002 |
| WO | WO 02/19922 | 3/2002 |
| WO | WO 02/19924 | 3/2002 |
| WO | WO 02/28286 | 4/2002 |
| WO | WO 02/38055 | 5/2002 |
| WO | WO 02/45593 | 6/2002 |
| WO | WO 02/45594 | 6/2002 |
| WO | WO 02/062234 | 8/2002 |
| WO | WO 02/098302 | 12/2002 |
| WO | WO 03/013363 | 2/2003 |
| WO | WO 03/013364 | 2/2003 |
| WO | WO 03/047434 | 6/2003 |
| WO | WO 03/071955 | 9/2003 |
| WO | WO 03/071956 | 9/2003 |
| WO | WO 03/071957 | 9/2003 |
| WO | WO 03/094748 | 11/2003 |
| WO | WO 03/101310 | 12/2003 |
| WO | WO 2004/004578 | 1/2004 |
| WO | WO 2004/012602 | 2/2004 |
| WO | WO 2004/060169 | 7/2004 |
| WO | WO 2004/069054 | 8/2004 |
| WO | WO 2005/000126 | 1/2005 |
| WO | WO 2005/006990 | 1/2005 |
| WO | WO 2005/041782 | 5/2005 |
| WO | WO 2005/063129 | 7/2005 |
| WO | WO 2005/082256 | 9/2005 |
| WO | WO 2005/092204 | 10/2005 |
| WO | WO 2005/110240 | 11/2005 |
| WO | WO 2005/112782 | 12/2005 |
| WO | WO 2005/115251 | 12/2005 |
| WO | WO 2005/115521 | 12/2005 |
| WO | WO 2006/000514 | 1/2006 |
| WO | WO 2006/026116 | 3/2006 |
| WO | WO 2006/052611 | 5/2006 |
| WO | WO 2006/052612 | 5/2006 |
| WO | WO 2006/078578 | 7/2006 |
| WO | WO 2006/083889 | 8/2006 |
| WO | WO 2006/115901 | 11/2006 |
| WO | WO 2006/115904 | 11/2006 |
| WO | WO 2006/118877 | 11/2006 |
| WO | WO 2007/005585 | 1/2007 |
| WO | WO 2007/025014 | 3/2007 |
| WO | WO 2007/081836 | 7/2007 |
| WO | WO 2007/088069 | 8/2007 |
| WO | WO 2008/031102 | 3/2008 |
| WO | WO 2008/036384 | 3/2008 |
| WO | WO 2008/074027 | 6/2008 |
| WO | WO 2008/150815 | 12/2008 |
| WO | WO 2009/079091 | 6/2009 |
| WO | WO 2010/062693 | 6/2010 |
| WO | WO 2010/081101 | 7/2010 |
| WO | WO 2010/081102 | 7/2010 |
| WO | WO 2010/081103 | 7/2010 |
| WO | WO 2010/081106 | 7/2010 |
| ZA | 200100527 | 1/2001 |
| ZA | 200100528 | 1/2001 |

OTHER PUBLICATIONS

U.S. Appl. No. 09/866,551, filed May 25, 2001, Ginn.
U.S. Appl. No. 12/113,092, filed Apr. 30, 2008, Ginn et al.
U.S. Appl. No. 12/548,274, filed Aug. 26, 2009, Clark.
U.S. Appl. No. 12/724,304, filed Mar. 15, 2010, Fortson.
U.S. Appl. No. 12/848,642, filed Aug. 2, 2010, Fortson et al.
U.S. Appl. No. 12/897,358, filed Oct. 4, 2010, Carley.
U.S. Appl. No. 12/941,809, filed Nov. 8, 2010, Ginn et al.
U.S. Appl. No. 12/950,628, filed Nov. 19, 2010, Walberg et al.
U.S. Appl. No. 12/955,859, filed Nov. 29, 2010, Ginn.
U.S. Appl. No. 12/961,331, filed Dec. 6, 2010, Voss.
U.S. Appl. No. 12/966,923, filed Dec. 13, 2010, Cummins et al.
U.S. Appl. No. 12/973,204, filed Dec. 20, 2010, Jabba et al.
U.S. Appl. No. 12/987,792, filed Jan. 10, 2011, Palermo et al.
U.S. Appl. No. 60/693,531, filed Jun. 24, 2005, Carly.
U.S. Appl. No. 60/696,069, filed Jul. 1, 2005, Pantages et al.
U.S. Appl. No. 60/793,444, filed Apr. 20, 2006, Jones et al.
U.S. Appl. No. 60/946,026, filed Jun. 25, 2007, Ellingwood.
U.S. Appl. No. 60/946,030, filed Jun. 25, 2007, Voss et al.
U.S. Appl. No. 60/946,042, filed Jun. 25, 2007, Ellingwood et al.
U.S. Appl. No. 61/015,144, filed Dec. 19, 2007, Mackiewicz et al.
U.S. Appl. No. 61/109,822, filed Oct. 30, 2008, Mehl et al.
U.S. Appl. No. 61/139,995, filed Dec. 22, 2008, Clark.
U.S. Appl. No. 61/141,597, filed Dec. 30, 2008, Clark.
U.S. Appl. No. 61/143,748, filed Jan. 9, 2009, Mehl et al.
U.S. Appl. No. 61/143,751, filed Jan. 9, 2009, Voss et al.
U.S. Appl. No. 61/145,468, filed Jan. 16, 2009, Fortson, et al.
"Hand tool for forming telephone connections—comprises pliers with reciprocably driven ram crimping clip around conductors against anvil", Derwent-ACC-No. 1978-B8090A.
Database WPI; Section PQ, Week 200120; Derwent Publications Ltd., London GB; AN 2001-203165; XP002199926 & ZA 200 100 528 A (Anthony T), Feb. 28, 2001 abstract.
Deepak Mital et al, Renal Transplantation Without Sutures Using the Vascular Clipping System for Renal Artery and Vein Anastomosis—A New Technique, Transplantation Issue, Oct. 1996, pp. 1171-1173, vol. 62—No. 8, Section of Transplantation Surgery, Department of General Surgery, Rush-Presbyterian/St. Luke's Medical Center, Chigago, IL.
DL Wessel et al, Outpatient closure of the patent ductus arteriosus, Circulation, May 1988, pp. 1068-1071, vol. 77—No. 5, Department of Anesthesia, Childrens's Hospital, Boston, MA.
E Pikoulis et al, Arterial reconstruction with vascular clips is safe and quicker than sutured repair, Cardiovascular Surgery, Dec. 1998, pp. 573-578(6), vol. 6—No. 6, Department of Surgery, Uniformed Services University of the Health Sciences, Bethesda, MD.
G Gershony et al, Novel vascular sealing device for closure of percutaneous vascular access sites, Cathet. Cardiovasc. Diagn., Jan. 1998, pp. 82-88, vol. 45.
H De Swart et al, A new hemostatic puncture closure device for the immediate sealing of arterial puncture sites, American journal of cardiology, Aug. 1993, pp. 445-449, vol. 72—No. 5, Department of Cardiology, Academic Hospital Maastricht, The Netherlands.
Harrith M. Hasson M.D. , Laparoscopic Cannula Cone with Means for Cannula Stabilization and Wound Closure, The Journal of the American Association of Gynecologic Laparoscopists, May 1998, pp. 183-185, vol. 5—No. 2, Division of Obstetrics and Gynecology, University of Chicago, Chicago, IL.
J. Findlay et al, Carotid Arteriotomy Closure Using a Vascular Clip System, Neurosurgery, Mar. 1998, pp. 550-554, vol. 42—No. 3, Division of Neurosurgery, University of Alberta, Edmonton, Canada.
Jeremy L Gilbert PhD, Wound Closure Biomaterials and Devices, Shock., Mar. 1999, p. 226, vol. 11—No. 3, Institution Northwestern University (editorial review).
Jochen T. Cremer, MD, et al, Different approaches for minimally invasive closure of atrial septal defects, Ann. Thorac. Surg., Nov. 1998, pp. 1648-1652, vol. 67, a Division of Thoracic and Cardiovascular Surgery, Surgical Center, Hannover Medical School. Hannover, Germany.
K Narayanan et al, Simultaneous primary closure of four fasciotomy wounds in a single setting using the Sure-Closure device, Injury, Jul. 1996, pp. 449-451, vol. 27—No. 6, Department of Surgery, Mercy Hospital of Pittsburgh, PA.
Marshall A.C., Lock J.E., Structural and Compliant Anatomy of the Patent Foramen Ovale in Patients Undergoing Transcatheter Closure, Am Heart J Aug. 2000; 140(2); pp. 303-307.

MD Gonze et al, Complications associated with percutaneous closure devices, Conference: Annual Meeting of the Society for Clinical Vascular Surgery, The American journal of surgery, Mar. 1999, pp. 209-211, vol. 178, No. 3, Department of Surgery, Section of Vascular Surgery, Ochsner Medical Institutions, New Orleans, LA.

MD Hellinger et al, Effective peritoneal and fascial closure of abdominal trocar sites utilizing the Endo-Judge, J Laparoendosc Surg., Oct. 1996, pp. 329-332, vol. 6—No. 5, Orlando Regional Medical Center, FL.

Michael Gianturco, A Play on Catheterization, Forbes, Dec. 1996, p. 146, vol. 158—No. 15.

Inlet Medical Inc. Brochure, pp. 1-2, referencing OM Elashry et al, Comparative clinical study of port-closure techniques following laparoscopic surgery, Department of Surgery, Mallickrodt Institute of Radiography, J Am Coll Surg., Oct. 1996, pp. 335-344, vol. 183—No. 4.

P M N Werker, et al, Review of facilitated approaches to vascular anastomosis surgery, Conference: Utrecht MICABG Workshop 2, The Annals of thoracic surgery, Apr. 1996, pp. S122-S127, vol. 63—No. 6, Department of Plastic, Reconstructive and Hand surgery, University Hospital Utrecht Netherlands Departments of Cardiology and Cardiopulmonary Surgery, Heart Lung Institute, Utrecht Netherlands.; Utrect University Hospital Utrecht Netherlands.

Peter Rhee MD et al, Use of Titanium Vascular Staples in Trauma, Journal of Trauma-Injury Infection & Critical Care, Dec. 1998, pp. 1097-1099, vol. 45—No. 6, Institution from the Department of Surgery, Washington Hospital Center, Washington DC, and Uniformed Services University of the Health Sciences, Bethesda, Maryland.

ProstarXL—Percutaneous Vascular Surgical Device, www.Archive.org, Jun. 1998, Original Publisher: http://prostar.com, may also be found at http://web.archive.org/web/19980630040429/www.perclose.com/html/prstrxl.html.

SA Beyer-Enke et al, Immediate sealing of arterial puncture site following femoropopliteal angioplasty: A prospective randomized trial, Cardiovascular and Interventional Radiology 1996, Nov.-Dec. 1996, pp. 406-410, vol. 19—No. 6, Gen Hosp North, Dept Dianost & Intervent Radiol, Nurnberg, Germany (Reprint).

Scott Hensley, Closing Wounds. New Devices seal arterial punctures in double time, Modern Healthcare (United States), Mar. 23, 2008, p. 48.

Sigmund Silber et al, A novel vascular device for closure of percutaneous arterial access sites, The American Journal of Cardiology, Apr. 1999, pp. 1248-1252, vol. 83—No. 8.

Simonetta Blengino et al, A Randomized Study of the 8 French Hemostatic Puncture Closure Device vs Manual Compression After Coronary Interventions, Journal of the American College of Cardiology, Feb. 1995, p. 262A, vol. 25.—No. 2, Supplement 1.

Stretch Comb by Scunci, retrieved via internet at www.scunci.com/productdetail by examiner on Oct. 9, 2007, publication date unavailable.

Swee Lian Tan, MD, PhD, FACS, Explanation of Infected Hemostatic Puncture Closure Devices—A Case Report, Vascular and Endovascular Surgery, 1999, pp. 507-510, vol. 33—No. 5, Parkland Medical Center, Derry, New Hampshire.

SY Nakada et al, Comparison of newer laparoscopic port closure techniques in the porcine model, J Endourol, Oct. 1995, pp. 397-401, vol. 9—No. 5, Department of Surgery/Urology, University of Wisconsin Medical School, Madison.

Taber's Cyclopedic Medical Dictionary, 18th Ed. 1997, pp. 747 and 1420.

Thomas P. Baum RPA-C et al, Delayed Primary Closure Using Silastic Vessel Loops and Skin Staples: Description of the Technique and Case Reports, Annals of Plastic Surgery, Mar. 1999, pp. 337-340, vol. 42—No. 3, Institution Department of Plastic and Reconstructive Surgery, Albert Einstein College of Medicine and Montefiore Medical Center, Bronx, NY.

Tomoaki Hinohara, Percutaneous vascular surgery (Prostar® Plus and Techstar® for femoral artery site closure), Interventional Cardiology Newsletter, May-Jul. 1997, pp. 19-22, pp. 24-28, vol. 5—No. 3-4.

UT Aker et al, Immediate arterial hemostasis after cardiac catheterization: initial experience with a new puncture closure device, Cathet Cardiovasc Diagn, Mar. 1994, pp. 228-232, vol. 33—No. 3, Missouri Baptist Medical Center, St. Louis.

Wei Qu et al, An absorbable pinned-ring device for microvascular anastomosis of vein grafts: Experimental studies, Microsurgery 1999, Mar. 1999, pp. 128-134, vol. 19—No. 3, Department of Orthopaedic Surgery, Hiroshima University School of Medicine, Hiroshima, Japan.

William G. Kussmaul III MD, et al., Rapid arterial hemostasis and decreased access site complications after cardiac catheterization and angioplasty: Results of a randomized trial of a novel hemostatic device, Journal of the American College of Cardiology, Jun. 1995, pp. 1685-1692, vol. 25—No. 7.

U.S. Appl. No. 09/478,179, Mail Date Nov. 6, 2000, Notice of Allowance.

U.S. Appl. No. 09/546,998, Mail Date May 6, 2002, Notice of Allowance.

U.S. Appl. No. 09/610,238, Mail Date Mar. 26, 2001, Notice of Allowance.

U.S. Appl. No. 09/610,238, Mail Date Sep. 5, 2001, Office Action.

U.S. Appl. No. 09/610,238, Mail Date Feb. 11, 2002, Notice of Allowance.

U.S. Appl. No. 09/680,837, Mail Date Jul. 9, 2002, Office Action.

U.S. Appl. No. 09/680,837, Mail Date Nov. 6, 2002, Office Action.

U.S. Appl. No. 09/680,837, Mail Date Mar. 25, 2003, Office Action.

U.S. Appl. No. 09/680,837, Mail Date Jun. 16, 2003, Notice of Allowance.

U.S. Appl. No. 09/732,178, Mail Date Aug. 1, 2002, Office Action.

U.S. Appl. No. 09/732,178, Mail Date Dec. 24, 2002, Office Action.

U.S. Appl. No. 09/732,178, Mail Date Jun. 10, 2003, Office Action.

U.S. Appl. No. 09/732,178, Mail Date Jul. 3, 2003, Office Action.

U.S. Appl. No. 09/732,178, Mail Date Nov. 17, 2003, Notice of Allowance.

U.S. Appl. No. 09/732,835, Mail Date Sep. 11, 2003, Office Action.

U.S. Appl. No. 09/732,835, Mail Date Feb. 9, 2004, Office Action.

U.S. Appl. No. 09/732,835, Mail Date Mar. 17, 2004, Notice of Allowance.

U.S. Appl. No. 09/764,813, Mail Date Mar. 26, 2001, Office Action.

U.S. Appl. No. 09/764,813, Mail Date Jun. 4, 2001, Notice of Allowance.

U.S. Appl. No. 09/933,299, Mail Date Feb. 26, 2003, Office Action.

U.S. Appl. No. 09/933,299, Mail Date Jun. 16, 2003, Notice of Allowance.

U.S. Appl. No. 09/948,813, Mail Date Jan. 31, 2003, Notice of Allowance.

U.S. Appl. No. 09/949,398, Mail Date Mar. 4, 2003, Office Action.

U.S. Appl. No. 09/949,398, Mail Date Jul. 28, 2003, Notice of Allowance.

U.S. Appl. No. 09/949,438, Mail Date Dec. 17, 2002, Office Action.

U.S. Appl. No. 09/949,438, Mail Date Apr. 21, 2003, Notice of Allowance.

U.S. Appl. No. 10/006,400, Mail Date Aug. 27, 2004, Office Action.

U.S. Appl. No. 10/006,400, Mail Date Feb. 23, 2005, Office Action.

U.S. Appl. No. 10/006,400, Mail Date Apr. 11, 2005, Office Action.

U.S. Appl. No. 10/006,400, Mail Date Jul. 27, 2005, Office Action.

U.S. Appl. No. 10/006,400, Mail Date Mar. 6, 2006, Office Action.

U.S. Appl. No. 10/006,400, Mail Date May 24, 2006, Office Action.

U.S. Appl. No. 10/006,400, Mail Date Oct. 26, 2006, Office Action.

U.S. Appl. No. 10/006,400, Mail Date Apr. 19, 2007, Office Action.

U.S. Appl. No. 10/006,400, Mail Date Apr. 2, 2008, Office Action.

U.S. Appl. No. 10/006,400, Mail Date Jan. 2, 2009, Office Action.

U.S. Appl. No. 10/006,400, Mail Date Jul. 9, 2009, Notice of Allowance.

U.S. Appl. No. 10/006,400, Mail Date Jan. 13, 2010, Notice of Allowance.

U.S. Appl. No. 10/006,400, Mail Date Apr. 27, 2010, Notice of Allowance.

U.S. Appl. No. 10/006,400, Mail Date Aug. 2, 2010, Notice of Allowance.

U.S. Appl. No. 10/081,717, Mail Date Sep. 29, 2003, Notice of Allowance.

U.S. Appl. No. 10/081,723, Mail Date Sep. 29, 2004, Office Action.

U.S. Appl. No. 10/081,723, Mail Date May 13, 2005, Notice of Allowance.

U.S. Appl. No. 10/081,725, Mail Date Feb. 9, 2004, Notice of Allowance.
U.S. Appl. No. 10/081,725, Mail Date Apr. 13, 2004, Office Action.
U.S. Appl. No. 10/081,726, Mail Date Apr. 11, 2003, Notice of Allowance.
U.S. Appl. No. 10/081,726, Mail Date Jun. 9, 2003, Notice of Allowance.
U.S. Appl. No. 10/147,774, Mail Date Nov. 4, 2004, Office Action.
U.S. Appl. No. 10/147,774, Mail Date May 4, 2005, Office Action.
U.S. Appl. No. 10/147,774, Mail Date Oct. 18, 2005, Office Action.
U.S. Appl. No. 10/147,774, Mail Date Apr. 18, 2007, Notice of Allowance.
U.S. Appl. No. 10/147,774, Mail Date Sep. 27, 2007, Notice of Allowance.
U.S. Appl. No. 10/147,774, Mail Date Feb. 4, 2008, Notice of Allowance.
U.S. Appl. No. 10/147,774, Mail Date Jun. 30, 2008, Office Action.
U.S. Appl. No. 10/147,774, Mail Date Mar. 18, 2009, Office Action.
U.S. Appl. No. 10/147,774, Mail Date Oct. 26, 2009, Office Action.
U.S. Appl. No. 10/147,774, Mail Date Jun. 8, 2010, Office Action.
U.S. Appl. No. 10/147,774, Mail Date Dec. 2, 2010, Notice of Allowance.
U.S. Appl. No. 10/240,183, Mail Date Jul. 27, 2004, Office Action.
U.S. Appl. No. 10/240,183, Mail Date Dec. 17, 2004, Office Action.
U.S. Appl. No. 10/240,183, Mail Date Mar. 9, 2005, Notice of Allowance.
U.S. Appl. No. 10/240,183, Mail Date Aug. 11, 2006, Amendment under 312.
U.S. Appl. No. 10/264,306, Mail Date Feb. 9, 2005, Office Action.
U.S. Appl. No. 10/264,306, Mail Date Oct. 4, 2005, Office Action.
U.S. Appl. No. 10/264,306, Mail Date May 10, 2006, Notice of Allowance.
U.S. Appl. No. 10/264,306, Mail Date Jul. 2, 2007, Notice of Allowance.
U.S. Appl. No. 10/264,306, Mail Date Feb. 4, 2008, Notice of Allowance.
U.S. Appl. No. 10/264,306, Mail Date Jun. 27, 2008, Office Action.
U.S. Appl. No. 10/264,306, Mail Date Feb. 26, 2009, Office Action.
U.S. Appl. No. 10/264,306, Mail Date Aug. 13, 2009, Office Action.
U.S. Appl. No. 10/264,306, Mail Date Jan. 27, 2010, Office Action.
U.S. Appl. No. 10/264,306, Mail Date Jun. 15, 2010, Office Action.
U.S. Appl. No. 10/264,306, Mail Date Oct. 29, 2010, Notice of Allowance.
U.S. Appl. No. 10/335,075, Mail Date Aug. 10, 2005, Office Action.
U.S. Appl. No. 10/335,075, Mail Date Dec. 19, 2005, Office Action.
U.S. Appl. No. 10/335,075, Mail Date Apr. 21, 2006, Office Action.
U.S. Appl. No. 10/335,075, Mail Date Dec. 27, 2006, Notice of Allowance.
U.S. Appl. No. 10/356,214, Mail Date Nov. 30, 2005, Office Action.
U.S. Appl. No. 10/356,214, Mail Date Aug. 23, 2006, Office Action.
U.S. Appl. No. 10/356,214, Mail Date Feb. 13, 2007, Office Action.
U.S. Appl. No. 10/356,214, Mail Date Sep. 12, 2007, Office Action.
U.S. Appl. No. 10/356,214, Mail Date Mar. 6, 2008, Office Action.
U.S. Appl. No. 10/356,214, Mail Date Nov. 4, 2008, Office Action.
U.S. Appl. No. 10/356,214, Mail Date Apr. 29, 2009, Office Action.
U.S. Appl. No. 10/356,214, Mail Date Jan. 13, 2010, Notice of Allowance.
U.S. Appl. No. 10/356,214, Mail Date May 13, 2010, Notice of Allowance.
U.S. Appl. No. 10/356,214, Mail Date Sep. 3, 2010, Notice of Allowance.
U.S. Appl. No. 10/435,104, Mail Date Jun. 10, 2004, Office Action.
U.S. Appl. No. 10/435,104, Mail Date Sep. 21, 2004, Notice of Allowance.
U.S. Appl. No. 10/435,104, Mail Date Jan. 3, 2006, Examiner's Amendment.
U.S. Appl. No. 10/435,104, Mail Date May 16, 2006, Office Action.
U.S. Appl. No. 10/435,104, Mail Date Dec. 28, 2006, Notice of Allowance.
U.S. Appl. No. 10/435,104, Mail Date Jul. 10, 2007, Notice of Allowance.
U.S. Appl. No. 10/435,104, Mail Date Aug. 2, 2007, Notice of Allowance.
U.S. Appl. No. 10/435,104, Mail Date Oct. 26, 2007, Notice of Allowance.
U.S. Appl. No. 10/435,104, Mail Date Nov. 14, 2007, Notice of Allowance.
U.S. Appl. No. 10/435,104, Mail Date Apr. 4, 2008, Notice of Allowance.
U.S. Appl. No. 10/435,104, Mail Date Sep. 26, 2008, Notice of Allowance.
U.S. Appl. No. 10/435,104, Mail Date Dec. 22, 2008, Notice of Allowance.
U.S. Appl. No. 10/435,104, Mail Date Jul. 23, 2009, Notice of Allowance.
U.S. Appl. No. 10/435,104, Mail Date Jan. 20, 2010, Notice of Allowance.
U.S. Appl. No. 10/435,104, Mail Date Jun. 2, 2010, Office Action.
U.S. Appl. No. 10/435,104, Mail Date Oct. 5, 2010, Notice of Allowance.
U.S. Appl. No. 10/455,768, Mail Date Nov. 16, 2004, Office Action.
U.S. Appl. No. 10/455,768, Mail Date Apr. 6, 2005, Notice of Allowance.
U.S. Appl. No. 10/486,067, Mail Date Jan. 10, 2006, Office Action.
U.S. Appl. No. 10/486,067, Mail Date Sep. 20, 2006, Notice of Allowance.
U.S. Appl. No. 10/486,070, Mail Date Apr. 20, 2005, Office Action.
U.S. Appl. No. 10/486,070, Mail Date Aug. 10, 2005, Office Action.
U.S. Appl. No. 10/486,070, Mail Date Oct. 18, 2005, Notice of Allowance.
U.S. Appl. No. 10/517,004, Mail Date Aug. 13, 2007, Office Action.
U.S. Appl. No. 10/517,004, Mail Date Jan. 30, 2008, Office Action.
U.S. Appl. No. 10/517,004, Mail Date Aug. 13, 2008, Notice of Allowance.
U.S. Appl. No. 10/517,004, Mail Date Feb. 10, 2009, Notice of Allowance.
U.S. Appl. No. 10/517,004, Mail Date Mar. 24, 2009, Notice of Allowance.
U.S. Appl. No. 10/517,004, Mail Date Jun. 26, 2009, Notice of Allowance.
U.S. Appl. No. 10/517,004, Mail Date Jan. 11, 2010, Notice of Allowance.
U.S. Appl. No. 10/517,004, Mail Date Apr. 23, 2010, Notice of Allowance.
U.S. Appl. No. 10/517,004, Mail Date Aug. 3, 2010, Notice of Allowance.
U.S. Appl. No. 10/517,004, Mail Date Nov. 23, 2010, Issue Notification.
U.S. Appl. No. 10/519,778, Mail Date Feb. 23, 2006, Office Action.
U.S. Appl. No. 10/519,778, Mail Date May 31, 2006, Notice of Allowance.
U.S. Appl. No. 10/541,083, Mail Date Oct. 16, 2007, Office Action.
U.S. Appl. No. 10/541,083, Mail Date Oct. 31, 2007, Office Action.
U.S. Appl. No. 10/541,083, Mail Date May 5, 2008, Office Action.
U.S. Appl. No. 10/541,083, Mail Date Sep. 19, 2008, Notice of Allowance.
U.S. Appl. No. 10/541,083, Mail Date Dec. 29, 2008, Notice of Allowance.
U.S. Appl. No. 10/541,083, Mail Date filed Apr. 16, 2009, Notice of Allowance.
U.S. Appl. No. 10/541,083, Mail Date Sep. 30, 2009, Notice of Allowance.
U.S. Appl. No. 10/541,083, Mail Date Feb. 5, 2010, Notice of Allowance.
U.S. Appl. No. 10/541,083, Mail Date May 10, 2010, Notice of Allowance.
U.S. Appl. No. 10/541,083, Mail Date Aug. 17, 2010, Notice of Allowance.
U.S. Appl. No. 10/541,083, Mail Date Dec. 1, 2010, Issue Notification.
U.S. Appl. No. 10/616,832, Mail Date Jun. 30, 2006, Office Action.
U.S. Appl. No. 10/616,832, Mail Date Oct. 20, 2006, Office Action.
U.S. Appl. No. 10/616,832, Mail Date May 29, 2007, Office Action.
U.S. Appl. No. 10/616,832, Mail Date Jan. 22, 2008, Office Action.
U.S. Appl. No. 10/616,832, Mail Date Sep. 17, 2008, Office Action.
U.S. Appl. No. 10/616,832, Mail Date Jul. 21, 2009, Office Action.

U.S. Appl. No. 10/616,832, Mail Date Jan. 11, 2010, Notice of Allowance.
U.S. Appl. No. 10/616,832, Mail Date May 12, 2010, Notice of Allowance.
U.S. Appl. No. 10/616,832, Mail Date Sep. 20, 2010, Notice of Allowance.
U.S. Appl. No. 10/617,090, Mail Date Mar. 22, 2005, Office Action.
U.S. Appl. No. 10/617,090, Mail Date Jul. 6, 2005, Notice of Allowance.
U.S. Appl. No. 10/617,090, Mail Date Oct. 5, 2005, Notice of Allowance.
U.S. Appl. No. 10/638,115, Mail Date Sep. 22, 2006, Office Action.
U.S. Appl. No. 10/638,115, Mail Date Jan. 31, 2007, Office Action.
U.S. Appl. No. 10/638,115, Mail Date Sep. 18, 2007, Office Action.
U.S. Appl. No. 10/638,115, Mail Date Feb. 7, 2008, Office Action.
U.S. Appl. No. 10/638,115, Mail Date Oct. 29, 2008, Office Action.
U.S. Appl. No. 10/638,115, Mail Date May 7, 2009, Notice of Allowance.
U.S. Appl. No. 10/638,115, Mail Date Dec. 1, 2009, Notice of Allowance.
U.S. Appl. No. 10/638,115, Mail Date Apr. 2, 2010, Notice of Allowance.
U.S. Appl. No. 10/638,115, Mail Date Aug. 13, 2010, Notice of Allowance.
U.S. Appl. No. 10/638,115, Mail Date Dec. 22, 2010, Issue Notification.
U.S. Appl. No. 10/667,144, Mail Date Sep. 19, 2006, Office Action.
U.S. Appl. No. 10/667,144, Mail Date May 2, 2007, Office Action.
U.S. Appl. No. 10/667,144, Mail Date Nov. 19, 2007, Office Action.
U.S. Appl. No. 10/667,144, Mail Date Dec. 5, 2007, Office Action.
U.S. Appl. No. 10/667,144, Mail Date May 12, 2008, Office Action.
U.S. Appl. No. 10/667,144, Mail Date Mar. 24, 2009, Office Action.
U.S. Appl. No. 10/667,144, Mail Date Nov. 23, 2009, Office Action.
U.S. Appl. No. 10/667,144, Mail Date Jun. 22, 2010, Office Action.
U.S. Appl. No. 10/669,313, Mail Date Oct. 31, 2005, Office Action.
U.S. Appl. No. 10/669,313, Mail Date Jan. 11, 2006, Notice of Allowance.
U.S. Appl. No. 10/669,313, Mail Date Jun. 28, 2006, Notice of Allowance.
U.S. Appl. No. 10/682,459, Mail Date Sep. 15, 2006, Office Action.
U.S. Appl. No. 10/682,459, Mail Date Apr. 18, 2007, Office Action.
U.S. Appl. No. 10/682,459, Mail Date Apr. 2, 2008, Office Action.
U.S. Appl. No. 10/682,459, Mail Date Dec. 4, 2008, Office Action.
U.S. Appl. No. 10/682,459, Mail Date Jun. 10, 2009, Office Action.
U.S. Appl. No. 10/682,459, Mail Date Dec. 23, 2009, Office Action.
U.S. Appl. No. 10/682,459, Mail Date Apr. 28, 2010, Office Action.
U.S. Appl. No. 10/682,459, Mail Date Oct. 12, 2010, Office Action.
U.S. Appl. No. 10/786,444, Mail Date Oct. 30, 2006, Office Action.
U.S. Appl. No. 10/786,444, Mail Date Apr. 17, 2007, Office Action.
U.S. Appl. No. 10/786,444, Mail Date Aug. 31, 2007, Office Action.
U.S. Appl. No. 10/786,444, Mail Date Apr. 24, 2008, Office Action.
U.S. Appl. No. 10/786,444, Mail Date Oct. 17, 2008, Office Action.
U.S. Appl. No. 10/786,444, Mail Date Jun. 18, 2009, Office Action.
U.S. Appl. No. 10/786,444, Mail Date Jan. 14, 2010, Office Action.
U.S. Appl. No. 10/787,073, Mail Date Nov. 30, 2006, Office Action.
U.S. Appl. No. 10/787,073, Mail Date Sep. 5, 2007, Office Action.
U.S. Appl. No. 10/787,073, Mail Date Feb. 22, 2008, Office Action.
U.S. Appl. No. 10/787,073, Mail Date Nov. 12, 2008, Office Action.
U.S. Appl. No. 10/787,073, Mail Date Aug. 13, 2009, Office Action.
U.S. Appl. No. 10/787,073, Mail Date Feb. 17, 2010, Notice of Allowance.
U.S. Appl. No. 10/787,073, Mail Date Aug. 25, 2010, Notice of Allowance.
U.S. Appl. No. 10/787,073, Mail Date Sep. 15, 2010, Issue Notification.
U.S. Appl. No. 10/908,721, Mail Date Oct. 19, 2006, Office Action.
U.S. Appl. No. 10/908,721, Mail Date Aug. 10, 2007, Office Action.
U.S. Appl. No. 10/908,721, Mail Date Jan. 25, 2008, Office Action.
U.S. Appl. No. 10/908,721, Mail Date Nov. 25, 2008, Office Action.
U.S. Appl. No. 10/908,721, Mail Date Jun. 23, 2009, Office Action.
U.S. Appl. No. 10/908,721, Mail Date Feb. 2, 2010, Office Action.
U.S. Appl. No. 11/048,503, Mail Date Mar. 13, 2009, Office Action.
U.S. Appl. No. 11/048,503, Mail Date Jun. 26, 2009, Office Action.
U.S. Appl. No. 11/048,503, Mail Date Jan. 11, 2010, Notice of Allowance.
U.S. Appl. No. 11/048,503, Mail Date Apr. 26, 2010, Notice of Allowance.
U.S. Appl. No. 11/048,503, Mail Date Jul. 30, 2010, Notice of Allowance.
U.S. Appl. No. 11/048,503, Mail Date Dec. 8, 2010, Issue Notification.
U.S. Appl. No. 11/113,549, Mail Date Feb. 6, 2007, Office Action.
U.S. Appl. No. 11/113,549, Mail Date May 30, 2007, Office Action.
U.S. Appl. No. 11/113,549, Mail Date Nov. 9, 2007, Office Action.
U.S. Appl. No. 11/113,549, Mail Date Apr. 16, 2008, Office Action.
U.S. Appl. No. 11/113,549, Mail Date Jul. 21, 2009, Office Action.
U.S. Appl. No. 11/113,549, Mail Date Jul. 6, 2010, Office Action.
U.S. Appl. No. 11/113,549, Mail Date Jan. 4, 2011, Office Action.
U.S. Appl. No. 11/152,562, Mail Date May 13, 2008, Office Action.
U.S. Appl. No. 11/152,562, Mail Date Feb. 13, 2009, Office Action.
U.S. Appl. No. 11/152,562, Mail Date Jul. 6, 2009, Office Action.
U.S. Appl. No. 11/152,562, Mail Date Mar. 31, 2010, Office Action.
U.S. Appl. No. 11/152,562, Mail Date Sep. 16, 2010, Notice of Allowance.
U.S. Appl. No. 11/198,811, Mail Date Aug. 26, 2008, Office Action.
U.S. Appl. No. 11/198,811, Mail Date Apr. 6, 2009, Office Action.
U.S. Appl. No. 11/198,811, Mail Date Sep. 22, 2009, Office Action.
U.S. Appl. No. 11/198,811, Mail Date Jun. 29, 2010, Notice of Allowance.
U.S. Appl. No. 11/198,811, Mail Date Oct. 20, 2010, Issue Notification.
U.S. Appl. No. 11/344,793, Mail Date Jan. 22, 2009, Office Action.
U.S. Appl. No. 11/344,868, Mail Date Mar. 25, 2009, Office Action.
U.S. Appl. No. 11/344,891, Mail Date Apr. 29, 2008, Office Action.
U.S. Appl. No. 11/344,891, Mail Date Dec. 8, 2008, Office Action.
U.S. Appl. No. 11/344,891, Mail Date Feb. 26, 2009, Office Action.
U.S. Appl. No. 11/344,891, Mail Date Oct. 7, 2009, Office Action.
U.S. Appl. No. 11/344,891, Mail Date May 7, 2010, Office Action.
U.S. Appl. No. 11/390,586, Mail Date Jun. 24, 2009, Office Action.
U.S. Appl. No. 11/390,586, Mail Date Jul. 6, 2010 Office Action.
U.S. Appl. No. 11/396,141, Mail Date May 22, 2009. Office Action.
U.S. Appl. No. 11/396,141, Mail Date Aug. 26, 2009, Office Action.
U.S. Appl. No. 11/396,141, Mail Date May 4, 2010, Office Action.
U.S. Appl. No. 11/396,731, Mail Date Feb. 13, 2009, Office Action.
U.S. Appl. No. 11/396,731, Mail Date May 22, 2009, Office Action.
U.S. Appl. No. 11/396,731, Mail Date Jun. 29, 2010, Office Action.
U.S. Appl. No. 11/406,203, Mail Date May 14, 2007, Office Action.
U.S. Appl. No. 11/406,203, Mail Date Jan. 29, 2008, Notice of Allowance.
U.S. Appl. No. 11/406,203, Mail Date May 23, 2008, Notice of Allowance.
U.S. Appl. No. 11/406,203, Mail Date Sep. 22, 2008, Notice of Allowance.
U.S. Appl. No. 11/406,203, Mail Date Mar. 3, 2009, Office Action.
U.S. Appl. No. 11/406,203, Mail Date Sep. 16, 2009, Office Action.
U.S. Appl. No. 11/406,203, Mail Date Jun. 18, 2010, Notice of Allowance.
U.S. Appl. No. 11/406,203, Mail Date Oct. 6, 2010, Issue Notification.
U.S. Appl. No. 11/411,925, Mail Date Jun. 6, 2007, Office Action.
U.S. Appl. No. 11/411,925, Mail Date Feb. 5, 2008, Office Action.
U.S. Appl. No. 11/411,925, Mail Dated Jan. 12, 2009, Office Action.
U.S. Appl. No. 11/411,925, Mail Date Sep. 10, 2009, Office Action.
U.S. Appl. No. 11/427,297, Mail Date Jan. 30, 2009, Office Action.
U.S. Appl. No. 11/427,297, Mail Date Sep. 15, 2009, Office Action.
U.S. Appl. No. 11/427,297, Mail Date Sep. 15, 2010, Office Action.
U.S. Appl. No. 11/427,309, Mail Date May 28, 2008, Office Action.
U.S. Appl. No. 11/427,309, Mail Date Jan. 2, 2009, Office Action.
U.S. Appl. No. 11/427,309, Mail Date Apr. 20, 2009, Office Action.
U.S. Appl. No. 11/427,309, Mail Date Nov. 6, 2009, Office Action.
U.S. Appl. No. 11/427,309, Mail Date Apr. 26, 2010, Office Action.
U.S. Appl. No. 11/427,309, Mail Date Nov. 15, 2010, Office Action.
U.S. Appl. No. 11/455,993, Mail Date Feb. 17, 2009, Office Action.
U.S. Appl. No. 11/455,993, Mail Date Dec. 16, 2009, Office Action.
U.S. Appl. No. 11/532,325, Mail Date Feb. 23, 2009, Office Action.
U.S. Appl. No. 11/532,325, Mail Date Jun. 17, 2009, Office Action.

U.S. Appl. No. 11/532,325, Mail Date Jan. 5, 2010, Office Action.
U.S. Appl. No. 11/532,576, Mail Date Mar. 1, 2010, Office Action.
U.S. Appl. No. 11/532,576, Mail Date Apr. 23, 2010, Office Action.
U.S. Appl. No. 11/532,576, Mail Date Oct. 13, 2010, Notice of Allowance.
U.S. Appl. No. 11/674,930, Mail Date Jan. 8, 2009, Office Action.
U.S. Appl. No. 11/674,930, Mail Date Jun. 4, 2009, Office Action.
U.S. Appl. No. 11/674,930, Mail Date Jan. 8, 2010, Office Action.
U.S. Appl. No. 11/675,462, Mail Date Dec. 10, 2009, Office Action.
U.S. Appl. No. 11/675,462, Mail Date Aug. 31, 2010, Office Action.
U.S. Appl. No. 11/744,089, Mail Date Nov. 26, 2008, Office Action.
U.S. Appl. No. 11/744,089, Mail Date Aug. 14, 2009, Office Action.
U.S. Appl. No. 11/757,108, Mail Date Nov. 25, 2009, Office Action.
U.S. Appl. No. 11/767,818, Mail Date Dec. 24, 2009, Office Action.
U.S. Appl. No. 11/767,818, Mail Date Mar. 22, 2010, Office Action.
U.S. Appl. No. 11/767,818, Mail Date Sep. 30, 2010, Office Action.
U.S. Appl. No. 11/852,190, Mail Date Jan. 24, 2010, Office Action.
U.S. Appl. No. 11/852,190, Mail Date Nov. 1, 2010, Office Action.
U.S. Appl. No. 11/958,281, Mail Date Sep. 2, 2010, Office Action.
U.S. Appl. No. 11/958,281, Mail Date Oct. 8, 2010, Office Action.
U.S. Appl. No. 11/958,295, Mail Date Aug. 27, 2009, Office Action.
U.S. Appl. No. 11/958,295, Mail Date May 25, 2010, Office Action.
U.S. Appl. No. 11/959,334, Mail Date Aug. 19, 2009, Office Action.
U.S. Appl. No. 11/959,334, Mail Date Jan. 12, 2010, Notice of Allowance.
U.S. Appl. No. 11/959,334, Mail Date Apr. 14, 2010, Notice of Allowance.
U.S. Appl. No. 11/959,334, Mail Date Jul. 23, 2010, Notice of Allowance.
U.S. Appl. No. 11/959,334, Mail Date Nov. 10, 2010, Issue Notification.
U.S. Appl. No. 12/106,928, Mail Date Jan. 23, 2009, Office Action.
U.S. Appl. No. 12/106,928, Mail Date Oct. 5, 2009, Office Action.
U.S. Appl. No. 12/106,928, Mail Date May 10, 2010, Office Action.
U.S. Appl. No. 12/106,928, Mail Date Oct. 25, 2010, Office Action.
U.S. Appl. No. 12/106,937, Mail Date Mar. 30, 2009, Office Action.
U.S. Appl. No. 12/106,937, Mail Date Nov. 18, 2009, Office Action.
U.S. Appl. No. 12/113,851, Mail Date Apr. 27, 2010, Office Action.
U.S. Appl. No. 12/113,851, Mail Date Jun. 24, 2010, Office Action.
U.S. Appl. No. 12/113,851, Mail Date Dec. 16, 2010, Office Action.
U.S. Appl. No. 12/114,031, Mail Date Oct. 5, 2010, Office Action.
U.S. Appl. No. 12/114,031, Mail Date Nov. 22, 2010, Office Action.
U.S. Appl. No. 12/114,091, Mail Date Oct. 27, 2010, Office Action.
U.S. Appl. No. 12/114,091, Mail Date Dec. 17, 2010, Office Action.
U.S. Appl. No. 12/402,398, Mail Date Mar. 9, 2010, Office Action.
U.S. Appl. No. 12/402,398, Mail Date May 20, 2010, Office Action.
U.S. Appl. No. 12/403,256, Mail Date Dec. 16, 2009, Office Action.
U.S. Appl. No. 12/403,256, Mail Date Mar. 30, 2010, Office Action.
U.S. Appl. No. 12/403,256, Mail Date Aug. 19, 2010, Notice of Allowance.
U.S. Appl. No. 12/403,256, Mail Date Nov. 23, 2010, Issue Notification.
U.S. Appl. No. 12/403,277, Mail Date Jul. 8, 2010, Office Action.
U.S. Appl. No. 12/403,277, Mail Date Oct. 12, 2010, Office Action.
U.S. Appl. No. 29/296,370, Mail Date Aug. 18, 2008, Office Action.
U.S. Appl. No. 29/296,370, Mail Date Dec. 2, 2008, Notice of Allowance.
U.S. Appl. No. 29/296,370, Mail Date Apr. 1, 2009, Notice of Allowance.
U.S. Appl. No. 29/296,370, Mail Date Feb. 10, 2010, Issue Notification.
U.S. Appl. No. 10/006,400, Mail Date Nov. 10, 2010, Issue Notification.
U.S. Appl. No. 10/435,104, Mail Date Jan. 12, 2011, Issue Notification.
U.S. Appl. No. 13/017,636, filed Jan. 31, 2011, Carley et al.
U.S. Appl. No. 13/026,989, filed Feb. 14, 2011, Cummins.
U.S. Appl. No. 13/030,922, filed Feb. 18, 2011, Cummins.
U.S. Appl. No. 13/039,087, filed Mar. 2, 2011, Palermo et al.
U.S. Appl. No. 11/532,576, Mail Date Mar. 16, 2011, Issue Notification.
U.S. Appl. No. 11/767,818, Mail Date Feb. 16, 2011, Office Action.
U.S. Appl. No. 11/852,190, Mail Date Mar. 2, 2011, Office Action.
U.S. Appl. No. 11/958,281, Mail Date Mar. 10, 2011, Office Action.
U.S. Appl. No. 12/122,603, Mail Date Mar. 3, 2011, Office Action.
U.S. Appl. No. 12/402,398, Mail Date Jan. 24, 2011, Office Action.
U.S. Appl. No. 10/147,774, Mail Date Apr. 6, 2011, Issue Notification.
U.S. Appl. No. 10/682,459, Mail Date Apr. 1, 2011, Notice of Allowance.
U.S. Appl. No. 11/396,731, Mail Date Mar. 22, 2011, Office Action.
U.S. Appl. No. 11/427,297, Mail Date Mar. 21, 2011, Office Action.
U.S. Appl. No. 12/403,277, Mail Date Mar. 31, 2011, Office Action.
U.S. Appl. No. 12/122,603, Mail Date Apr. 22, 2011, Office Action.
U.S. Appl. No. 12/113,851, Mail Date Apr. 27, 2011, Office Action.
U.S. Appl. No. 12/481,377, Mail Date Apr. 28, 2011, Office Action.
U.S. Appl. No. 12/114,031, Mail Date May 11, 2011, Office Action.
U.S. Appl. No. 12/143,020, Mail Date May 11, 2011, Office Action.
U.S. Appl. No. 13/112,618, filed May 20, 2011, Gianotti et al.
U.S. Appl. No. 13/112,631, filed May 20, 2011, Voss.
U.S. Appl. No. 12/955,859, filed May 26, 2011, Office Action.
U.S. Appl. No. 13/153,594, filed Jun. 6, 2011, Reyes et al.
U.S. Appl. No. 10/667,144, Mail Date Jun. 6, 2011, Office Action.
U.S. Appl. No. 12/481,377, Mail Date Jun. 21, 2011, Office Action.
U.S. Appl. No. 13/222,899, filed Aug. 31, 2011, Carley et al.
U.S. Appl. No. 11/396,731, Mail Date Sep. 1, 2011, Office Action.
U.S. Appl. No. 11/675,462, Mail Date Aug. 3, 2011, Office Action.
U.S. Appl. No. 12/114,031, Mail Date Aug. 2, 2011, Office Action.
U.S. Appl. No. 12/114,091, Mail Date Jul. 7, 2011, Office Action.
U.S. Appl. No. 12/122,603, Mail Date Sep. 23, 2011, Office Action.
U.S. Appl. No. 12/135,858, Mail Date Jul. 13, 2011, Office Action.
U.S. Appl. No. 12/143,020, Mail Date Aug. 31, 2011, Office Action.
U.S. Appl. No. 12/393,877, Mail Date Sep. 29, 2011, Office Action.
U.S. Appl. No. 12/897,358, Mail Date Aug. 22, 2011, Office Action.
U.S. Appl. No. 12/955,859, Mail Date Jul. 21, 2011, Office Action.
U.S. Appl. No. 13/026,989, Mail Date Sep. 16, 2011, Office Action.
U.S. Appl. No. 12/684,569, Mail Date Jan. 27, 2012, Office Action.
U.S. Appl. No. 11/767,818, Mail Date Feb. 3, 2012, Notice of Allowance.
U.S. Appl. No. 12/684,542, Mail Date Jan. 30, 2012, Office Action.
U.S. Appl. No. 12/941,809, Mail Date Jan. 30, 2012, Office Action.
U.S. Appl. No. 12/966,923, Mail Date Feb. 3, 2012, Notice of Allowance.
U.S. Appl. No. 10/667,144, Mail Date Oct. 28, 2011, Notice of Allowance.
U.S. Appl. No. 11/675,462, Mail Date Dec. 22, 2011, Notice of Allowance.
U.S. Appl. No. 12/393,877, Mail Date Dec. 13, 2011, Office Action.
U.S. Appl. No. 12/481,377, Mail Date Jan. 3, 2012, Office Action.
U.S. Appl. No. 12/548,274, Mail Date Dec. 28, 2011, Restriction Requirement.
U.S. Appl. No. 12/684,470, Mail Date Dec. 20, 2011, Restriction Requirement.
U.S. Appl. No. 12/684,562, Mail Date Dec. 28, 2011, Restriction Requirement.
U.S. Appl. No. 12/684,569, Mail Date Dec. 20, 2011, Restriction Requirement.
U.S. Appl. No. 12/941,809, Mail Date Dec. 13, 2011, Restriction Requirement.
U.S. Appl. No. 12/955,859, Mail Date Dec. 15, 2011, Office Action.
U.S. Appl. No. 12/338,977, Mail Date Jan. 19, 2012, Office Action.
U.S. Appl. No. 12/897,358, Mail Date Jan. 12, 2012, Notice of Allowance.
U.S. Appl. No. 12/608,769, Mail Date Feb. 10, 2012, Office Action.
U.S. Appl. No. 12/684,400, Mail Date Feb. 13, 2012, Office Action.
U.S. Appl. No. 12/724,304, Mail Date Feb. 10, 2012, Office Action.
U.S. Appl. No 12/113,851, Mail Date Mar. 29, 2012, Office Action.
U.S. Appl. No. 12/114,091, Mail Date Apr. 5, 2012, Office Action.
U.S. Appl. No. 12/688,065, Mail Date Mar. 13, 2012, Office Action.
U.S. Appl. No. 12/987,792, Mail Date Mar. 13, 2012, Office Action.
U.S. Appl. No. 12/897,358, Mail Date May 2, 2012, Issue Notification.

* cited by examiner

METHODS FOR MANUFACTURING A CLIP AND CLIP

CROSS-REFERENCE TO RELATED APPLICATIONS

This application is a divisional of U.S. patent application Ser. No. 12/403,256, filed Mar. 12, 2009, and entitled "Methods for Manufacturing a Clip and Clip", which is a divisional of U.S. patent application Ser. No. 10/541,083, filed Jun. 29, 2005, and entitled "Methods for Manufacturing a Clip and Clip," which is a National Stage Application under 35 U.S.C. §371 of PCT/US03/40812, filed Dec. 17, 2003, and entitled "Methods for Manufacturing a Clip and Clip," which claims the benefit of U.S. patent application Ser. No. 10/335,075, filed Dec. 31, 2002, and entitled "Methods for Manufacturing a Clip and Clip," now issued as U.S. Pat. No. 7,211,101, the entireties of which are hereby incorporated by reference. This application incorporates U.S. Pat. No. 4,665,906, issued May 19, 1987, and entitled "Medical Devices Incorporating Sim Alloy Elements;" U.S. Pat. No. 6,719,777, issued Apr. 13, 2004, and entitled "Closure Device and Methods for Making and Using Them;" U.S. patent application Ser. No. 10/081,273, filed Feb. 21, 2002, and entitled "Multiple Use Handle Support for Distributing Forces;" U.S. patent application Ser. No. 10/081,726, filed Feb. 21, 2002, and entitled "Closure Device and Methods for Making and Using Them;" and U.S. patent application Ser. No. 10/081,717, filed Feb. 21, 2002, and entitled "Plunger Apparatus and Methods for Delivering a Closure Device," the entireties of which are incorporated herein by reference.

BACKGROUND OF THE INVENTION

The Field of the Invention

The use of certain types of clips, which are initially generally planar and which are deformed to non-planar configuration prior to use, to close openings through tissue, e.g., into body lumens, and more particularly to close a puncture made to gain access to a blood vessel or other body lumen is known. Such clips are generally annular and have tines extending radially from an annular body. For example, such clips are disclosed in the aforementioned co-pending applications and in published PCT Applications WO/99/62408, WO/00/56223 and WO/00/56227, the disclosures of which are incorporated by reference herein. Various methods, e.g., stamping, laser cutting, chemical etching and the like have been used to form the clips from a sheet of metal. Conventional manufacturing methods are limited with regard to minimizing the space between the tines because the necessary manufacturing tolerances require that sufficient space be allowed for the manufacturing tools and/or processing materials.

Improved methods of manufacturing these types of clips and the clips resulting from them would make such clips more effective for many such uses.

SUMMARY OF THE INVENTION

The present invention is directed to methods for manufacturing tissue engaging clips in a manner in which a clip-precursor is first formed and such precursor is then reconfigured into the final shape of the clip. In a preferred embodiment of the invention, a clip having an annular or hoop-shaped generally planar configuration with radially inwardly extending tines is manufactured by first forming a precursor with the tines extending radially outward and then reconfigured by inserting the precursor to its final shape with the tines extending radially inward and then heat setting the clip in this configuration. This permits the tines to be packed more closely together which enhances the sealing function of the clip and reduces the size of the clip's footprint. As will be explained in more detail herein, this manufacturing method overcomes the limitations of conventional methods in which the clip is manufactured in its final configuration.

In another preferred embodiment, an annular or hoop-shaped planar clip precursor with radially inwardly extending tines is first manufactured in an oversize configuration and then has its lateral dimensions reduced to pack the tines closer together and to reduce the footprint of the clip and then heat set in that configuration.

BRIEF DESCRIPTION OF THE DRAWINGS

To further clarify the above-recited and other advantages and features of the present invention, a more particular description of the invention will be rendered by reference to specific embodiments thereof which are illustrated in the appended drawings. It is appreciated that these drawings depict only typical embodiments of the invention and are therefore not to be considered limiting of its scope. The invention will be described and explained with additional specificity and detail through the use of the accompanying drawings in which.

DETAILED DESCRIPTION OF THE INVENTION

The clips manufactured according to the present invention are useful for engaging tissue so as to connect tissue segments together or to close and/or seal openings through tissue such as a puncture wound in a body lumen. These clips may be used by deforming them from their generally planar configuration such that the tines are pointing in a direction generally transverse to the plane, holding the clip in this deformed condition, deploying the clip proximal to the tissue to be engaged and removing the deforming force such that the clip engages the tissue and attempts to return to its original generally planar configuration. The methods and apparatus disclosed in the above-mentioned U.S. patent application Ser. Nos. 10/081,726 and 09/732,178 can be used to deploy the clips of the present invention to engage tissue and close or seal an opening.

In such use, the deformation of the clip causes the tines to be directed generally axially away from the body of the clip and it is the elastic property of the deformed clip which causes it to attempt to return to its original generally planar configuration. The body of the device may comprise a series of looped elements which generally define an endless zigzag pattern, e.g., a sinusoidal pattern, extending about a central access. The looped elements are believed to facilitate deforming the device between the planar and transverse configurations, e.g., by distributing stresses through the device and minimizing localized stresses in the curved regions.

In a first preferred embodiment of the present invention, a clip precursor is first formed from a sheet of material, preferably a superelastic alloy, such as a nickel-titanium alloy ("Nitinol") alloy. The property of superelasticity and of certain alloys which possess that property is disclosed in U.S. Pat. No. 4,665,906 which is incorporated by reference herein.

Figure 1A:
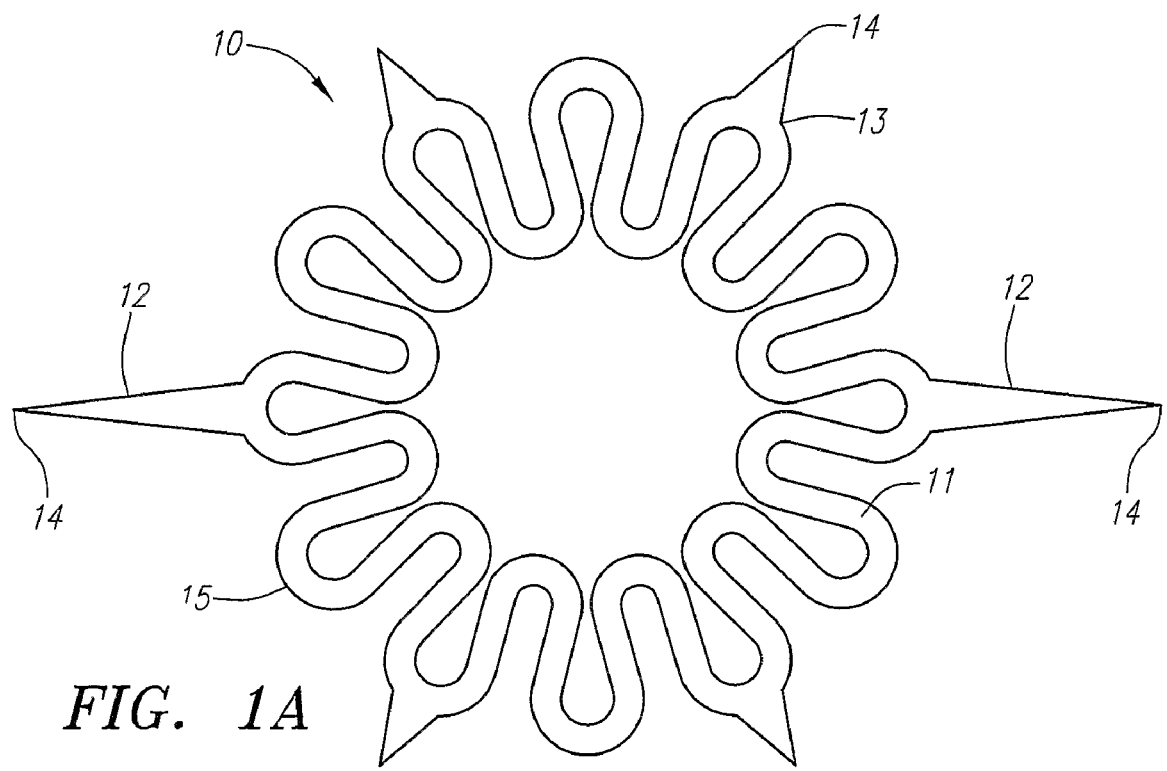
FIGS. 1A and 1B illustrate the before and after configuration of a clip manufactured according to one embodiment of this invention.

This forming can be done by removing portions of the material by cutting, chemical etching, laser cutting, photochemical etching, stamping, electrical discharge machining and the like to produce a precursor such as that shown in FIG. 1A which has radially outward extending tines.

The precursor can then be polished using one or more processes such as electropolishing, tumbling, sand blasting, sanding and the like or such polishing can be done as a final step after the clip is formed. Forming of a precursor in this manner does not require working to tolerances as close as those which would be required if the clip was to be manufactured in its final configuration shown in FIG. 1B because the radially outwardly extending tines of the precursor shown in FIG. 1A are easily accessible by the forming tool whereas attempting to directly form the clip with radially inwardly extending tines which are closely spaced requires difficult high precision metal cutting. Thus, manufacture of a precursor which is then reconfigured to final clip shape permits the achievement of closer spacing between the elements of the final clip than would otherwise be achievable with conventional methods.

The precursor 10 comprises a hoop-shaped planar body 11 which has outwardly extending primary (longer) tines 12 and secondary (shorter) tines 13. For example, the primary tines may be 0.070 to 0.105 inches in length and the secondary tines may be 0.025 to 0.035 inches in length. Each of the tines terminates in a point 14. When the precursor 10 has been reconfigured into clip 16 shown in FIG. 1B, the tines 12 and 13 become the tissue engaging portions of the clip. The tines may be sharpened or given a shape, e.g., barbs (not shown), while the device is in the precursor state. The body 11 may compromise connecting links such as loops 15. These links may have any suitable shape provided that such shape does not interfere with inversion of the precursor 10.

The precursor 10 is then inverted to reconfigure it into the shape of clip 16. In this preferred embodiment in which the precursor is formed from a sheet of nickel-titanium alloy, the inverted precursor is then heat set, e.g., by heating to a temperature of 510° C., and then quenched to cool to room temperature. The clip 16 will now be in the austenitic state.

Heat setting and quenching are essential to successful practice of the invention with superelastic alloys. As explained in more detail in U.S. Pat. No. 4,665,906, a superelastic alloy such as nickel-titanium exists in two states, the austenitic state and the martensitic state.

Such alloys will initially be in the austenitic state, e.g., when the precursor is formed.

However, when the precursor is inverted to take the shape of the final clip, the stress experienced by the alloy during the inversion will cause the alloy to be partially or wholly converted to the martensitic state. Such a martensitic state is commonly referred to as stress-induced martensite. Such martensite structure has the property of superelasticity and the inverted precursor would revert to its original shape if not held in the inverted configuration.

Figure 1B:
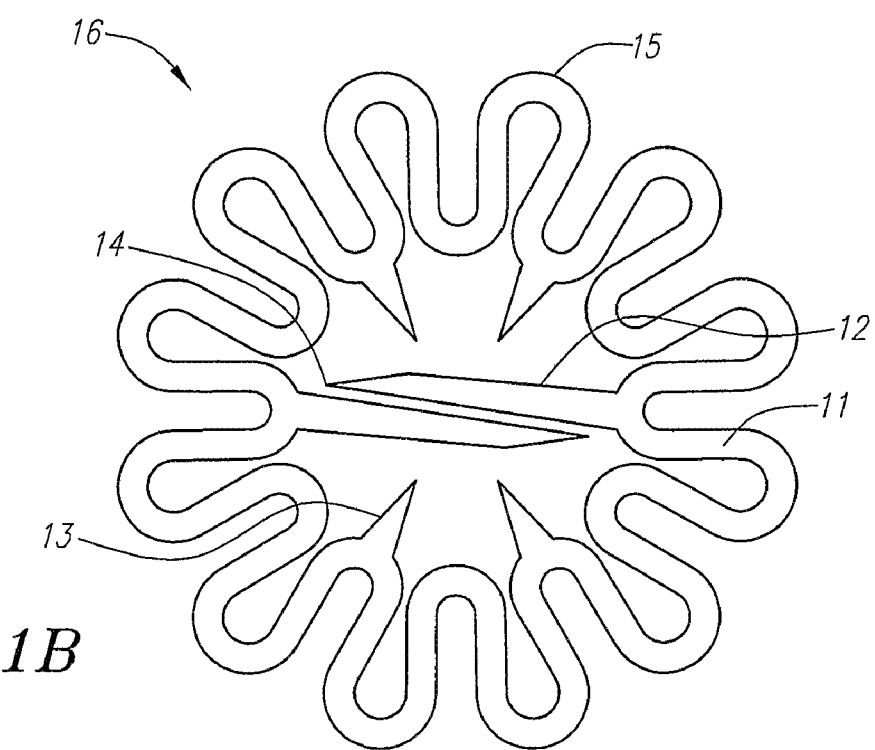

Since, if the inverted precursor was left in the martensitic state, it would want to elastically revert to its original uninverted state, it must be converted back to austenite. Thus, heating and quenching are required to convert the inverted precursor from the martensitic state to the austenitic state such that the clip is stable in its planar configuration as shown in FIG. 1B and will retain that configuration.

The times and temperatures for heat setting of superelastic alloys of various compositions can be determined from existing literature or can be determined empirically without any difficulty. The clips are small in size and the heating and quenching may be done with any conventional heating and quenching equipment. For example, once inverted, the inverted precursor can be held in that configuration and placed in a fixture which will hold it in the inverted configuration during heat setting.

When clips are manufactured according to the present invention, the space between the tines may actually be eliminated, i.e., after inverting the precursor, the tines may be in contact with each other, in either a side-by-side or an over-and-under relationship. The number, length and spacing of the tines may be varied according to the desires of the manufacturer.

Furthermore, while use of a planar precursor is a convenience in manufacturing, a planar configuration is not required. For example, the precursor could be bent along a diameter or major or minor axis of the precursor and could be heat set in such a bent configuration.

Figure 4:
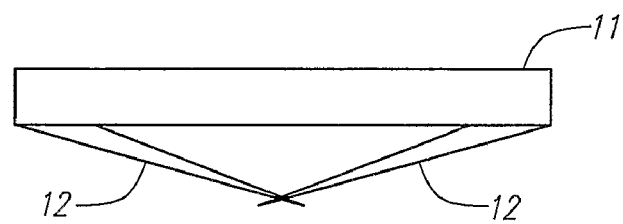
FIG. 4 illustrates a clip which, while generally planar, has tines which extend radially inwardly at an angle to the plane defined by the body.

Alternatively, the clip, while generally planar, may have the tines extending at an acute angle to the plane defined by the body as shown in FIG. 4 in which the body 11 and tines 12 are shown. Furthermore, manufacturing from a sheet of material is a convenience, but other manufacturing techniques, including joining of components such as the tines to the body, can be accomplished by welding, brazing, or other known methods of joining materials. In such cases, one or more of such components may be circular in cross-section or tubular in configuration.

Still further, the clip need not be fabricated from a single material, e.g., the tines may be manufactured from a different material than the body. In such cases, a portion of the clip such as the tines may be bioabsorbable provided that the final clip is capable of elastic recovery after being deformed. An advantage of the present invention is that it permits the production of clips with tines that are 30 to 40% or more longer than those which could be made with prior direct cutting methods, because there is no limit on the length of the tine which is formed on the precursor. Thus, after the precursor is inverted, the tines may overlap the annular body.

Figure 2A:
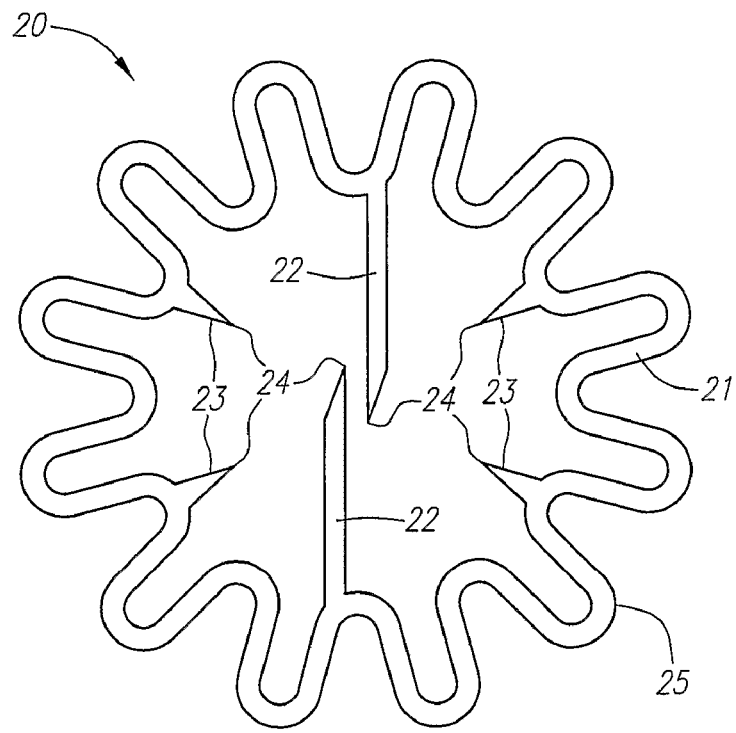
FIGS. 2A AND 2B illustrate the before and after-configuration of a clip manufactured according to another embodiment of the invention.
Figure 2B:
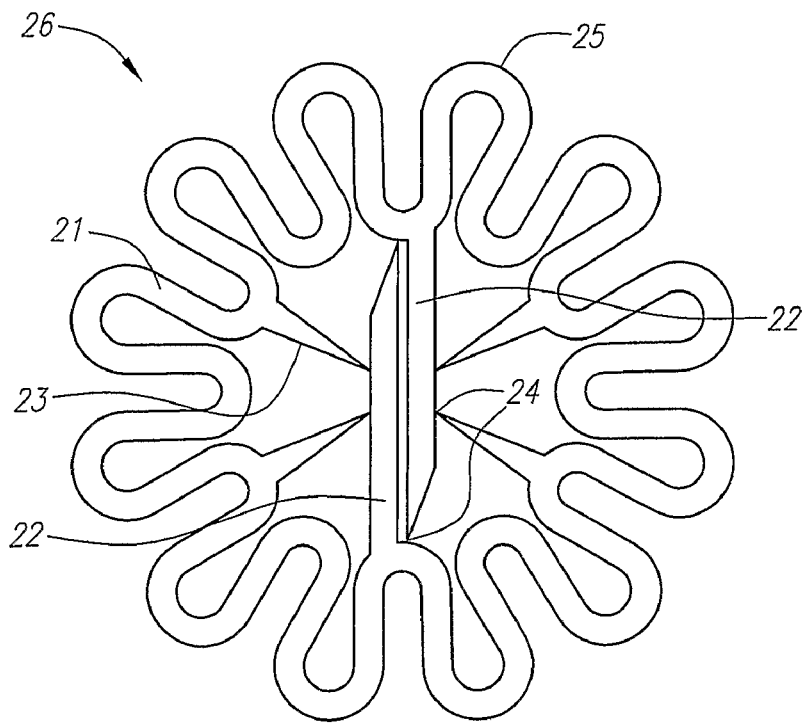

In the alternative embodiment of this invention illustrated in FIGS. 2A and 2B, the precursor 20 is manufactured in an expanded oversize configuration to provide space for removing material from a sheet of material, preferably a superelastic alloy such as nickel-titanium, by conventional methods such as cutting, chemical etching, photochemical etching, stamping, electric discharge machining, laser cutting or the like.

The precursor 20 is reconfigured by imposing radially inwardly directed force on body 21 such that precursor 20 takes a smaller planar shape such as one of those shown in FIG. 2B.

The precursor 20 has a planar body 21, tines 22 and 23 having points 24 and such tines are connected by links 25 as previously described with regard to FIG. 1A. The reconfigured precursor is then heat set and quenched as described above to complete the manufacture of clip 26.

Figure 3A:
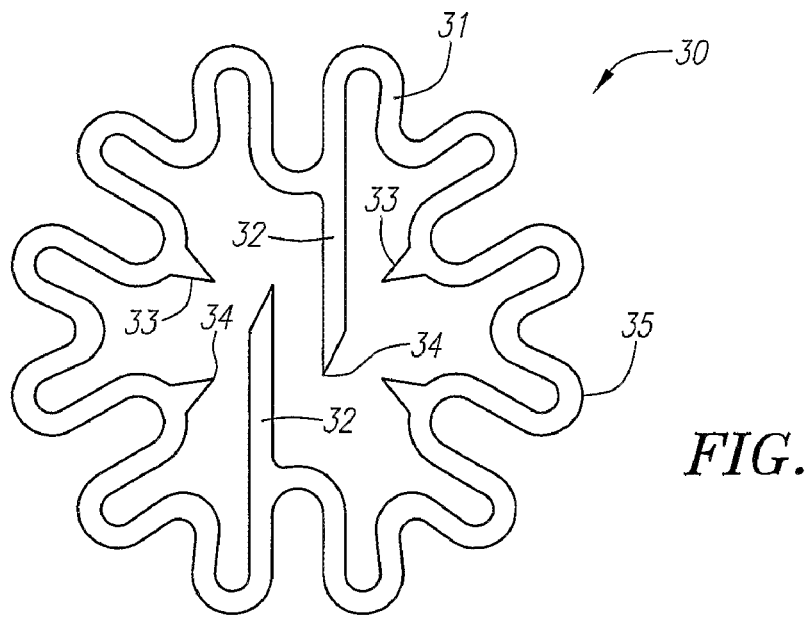
FIG. 3A-3C illustrate alternate before and after-configurations of clips manufactured according to the method of this invention in which the before configuration is that of FIG. 2A.
Figure 3B:
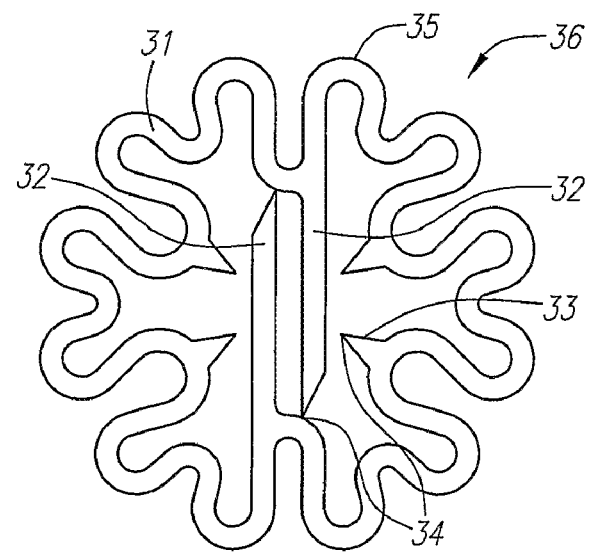
Figure 3C:
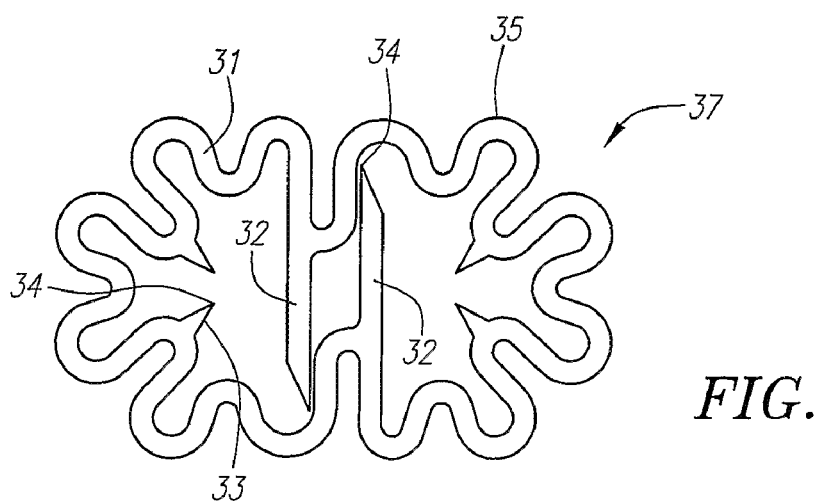

Clips of still other configurations can be manufactured in the manner of clip 26 by starting with a differently shaped precursor such as precursor 30 shown in FIG. 3A. Precursor 30 can be reconfigured by being subjected to radially inward deforming forces as shown in FIG. 3B or by opposed laterally inward forces as shown in FIG. 3C. In each case, the planar body 31 having tines 32 and 33 with points 34 and links 35 will be caused to take a smaller dimension and will be heat set as described above to form clips 36 and 37. Clips manufactured according to the method of the present invention can have a multitude of configurations other than those shown in FIGS. 1B, 2B, and 3B-3C. For example, the configurations shown in U.S. patent application Ser. Nos. 09/732,178 and 10/081,726 could be manufactured according to the present invention.

Figure 7:
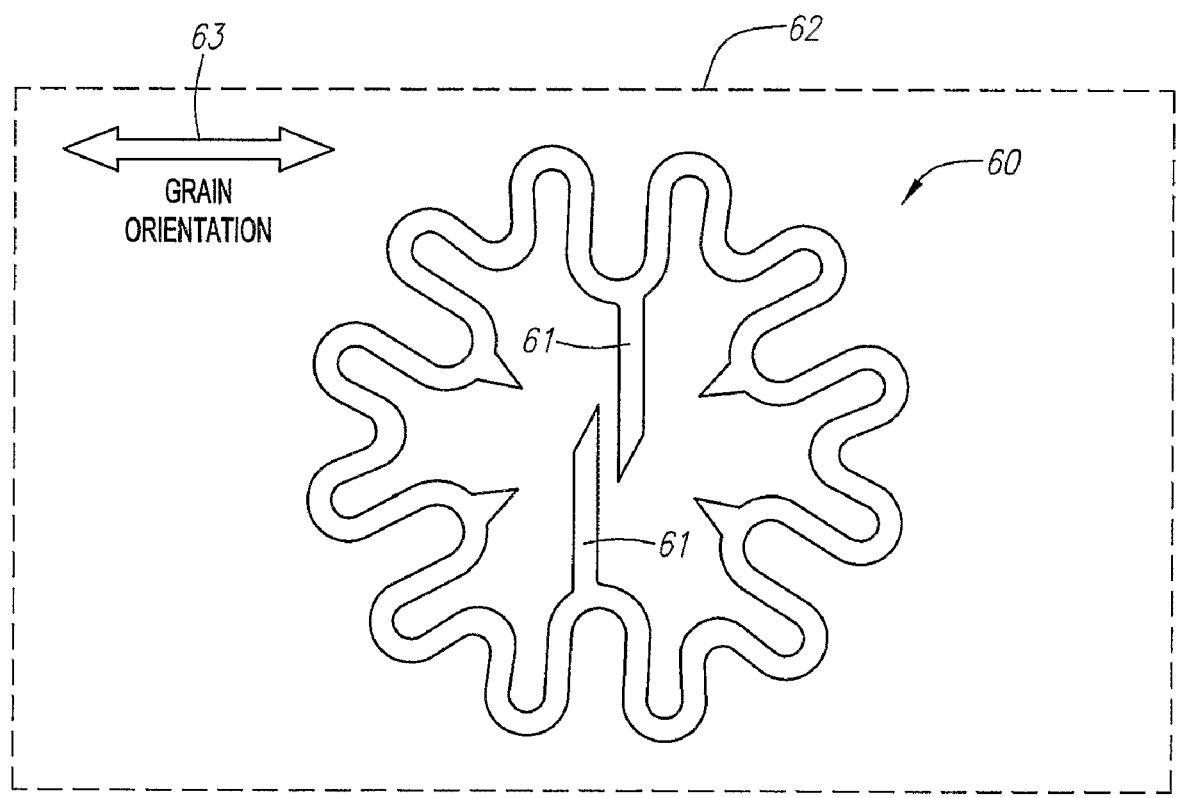
FIG. 7 illustrates the preferred relationship between the grain orientation of a nitinol sheet and the primary tines of a clip precursor.

It has been found that nitinol sheet is stronger in one direction than in others, which may be the result of crystal orientation in the nitinol. It is preferred to form the clip precursors such that the primary tines are aligned with the strongest orientation of the nitinol. It has been found, as shown in FIG. 7, that the greatest strength of the primary tines is achieved if those tines are transverse to the grain orientation of the nitinol. Thus, FIG. 7 illustrates clip precursor 60 having primary tines 61 as the precursor would be cut from sheet 62. The grain orientation of sheet 62 is shown by the double-headed arrow 63. Typically, a plurality of precursors 60 would be cut from the same sheet, each with its primary tines transverse to the grain orientation of the sheet. In addition, even if clips are formed directly without using precursors, it is desirable that their primary tines be transverse to the grain orientation.

Figure 5:
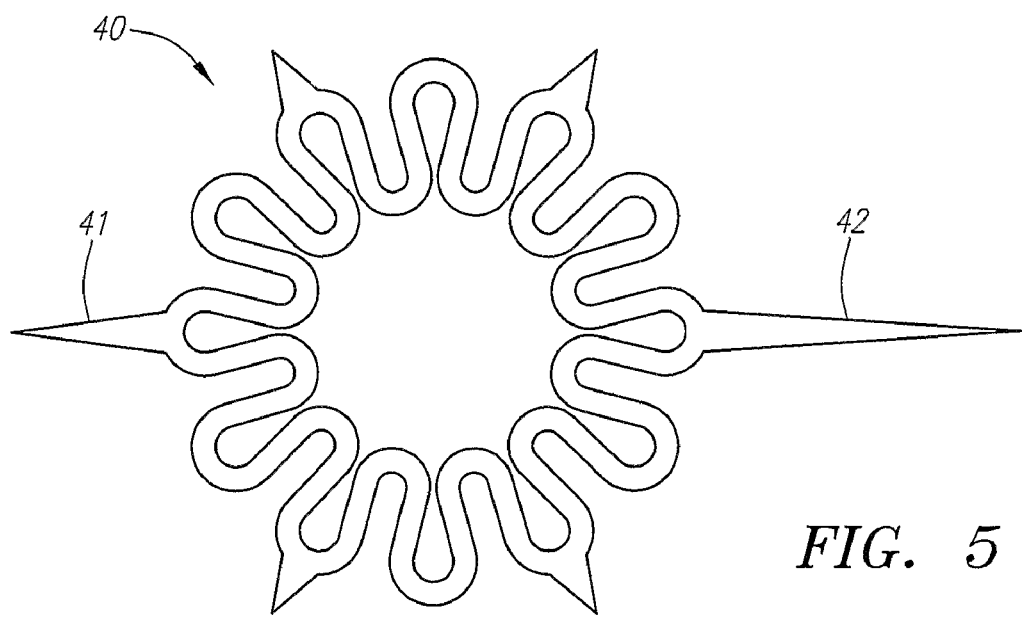
FIGS. 5 and 6 illustrate clip precursors in which radially opposed primary tines have different lengths.
Figure 6:
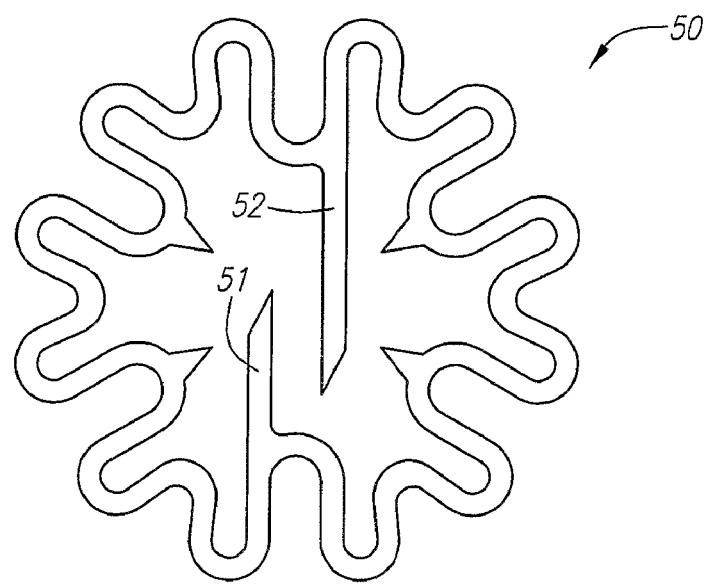

The clips of the present invention may have primary or secondary tines which have the same or different lengths and the tines may be straight or curved. For example, radially opposed tines may have one tine at "12 o'clock" which is longer than the opposing tine at "6 o'clock." Exemplary configurations of clip precursors with primary tines of different length are shown in FIGS. 5 and 6. In FIG. 5, clip precursor 40 is shown with a primary tine 41 which is shorter than primary tine 42. Similarly, in FIG. 6, a clip precursor 50 is shown which has a primary tine 51 which is shorter than primary tine 52.

The clips of the present invention may also be delivered using the apparatus and methods described in U.S. patent application Ser. No. 10/081,273, filed Feb. 21, 2002 which is assigned to the assignee of the present application and the disclosure of which is incorporated by reference herein. Similarly, the apparatus and methods disclosed in U.S. patent application Ser. No. 10/081,717, filed Feb. 21, 2002, which is assigned to the Assignee of the present application and the disclosure of which is incorporated by reference herein, may be used.

Other features can be added to the clips including radio-opaque markers, and/or porous surfaces to promote tissue ingrowth or the clip may be coated in whole or in part with a bioabsorbable material and/or coated with a material containing a substance which is delivered to the patient for therapeutic, diagnostic or other purposes. Such coatings may comprise peptides, clotting factors or other materials designed to benefit the patient.

While the principal object of the present invention is to provide a manufacturing method which facilitates the production of clips having a small footprint, the present invention can also be used to make clips of larger dimensions since, no matter what methods are used to cut the precursor from a sheet of material, the ease of manufacture of even larger size clips is facilitated. Thus, the advantages of the present invention may be realized with regard to clips having larger sizes and clips having a variety of configurations.

Having fully described the present invention including a description of preferred embodiments, it is to be understood that the scope of this invention is not to be limited to those preferred embodiments, but is of the full scope of the appended claims.

What is claimed is:

1. A clip manufactured according to the method of manufacturing a clip comprising the steps of:
    forming the precursor of a clip from a material comprising a superelastic alloy which has an austenitic state and a martensitic state, said precursor having a substantially annular body which is substantially planar and having a plurality of tines which extend radially outwardly from said body;
    inverting said precursor such that said tines extend radially inwardly and said precursor is in a substantially planar configuration, a first tine of the plurality of tines extending beyond a central axis of said body when in the substantially planar configuration, the central axis of the clip being perpendicular to a plane formed by the clip in the substantially planar configuration;
    heating said precursor in its inverted configuration to cause said alloy to become substantially austenitic; and
    quenching said heated precursor to form a clip which is substantially austenitic in the substantially planar configuration with at least two tines of the plurality of tines being in over-and-under, overlapping relationship in the substantially planar configuration.

2. The clip of claim 1 wherein said alloy is nickel-titanium.

3. The clip of claim 1 wherein said body comprises a plurality of looped elements.

4. The clip of claim 1 wherein at least one tine is longer than a radially opposed tine.

5. The clip of claim 1 wherein said forming step comprises cutting said precursor from a sheet of material comprising a superelastic alloy.

6. A clip manufactured according to the method of manufacturing a clip comprising the steps of:
    forming the precursor of a clip from a material comprising a superelastic alloy which has an austenitic state and a martensitic state, said precursor having a substantially annular body which is substantially planar and having a plurality of tines which extend radially inwardly from said body, said precursor having a lateral dimension which is substantially larger than that of the clip;
    compressing said precursor in a substantially planar configuration in a radially inward direction to bring said tines closer together with at least two tines of the plurality of tines being parallel and each of the at least two tines of the plurality of tines extending beyond a central axis of the clip while in the substantially planar configuration, the central axis of the clip being perpendicular to a plane formed by the clip in the substantially planar configuration;
    heating said precursor in its compressed and substantially planar configuration to cause said alloy to become substantially austenitic; and
    quenching said heated precursor to form a clip which is substantially austenitic.

7. The clip of claim 6 wherein said alloy is nickel-titanium.

8. The clip of claim 6 wherein said body comprises a plurality of looped elements.

9. The clip of claim 6 wherein said forming step comprises cutting said precursor from a sheet of material comprising a superelastic alloy.

10. The clip of claim 6 wherein at least one tine is longer than a radially opposed tine.

11. A clip manufactured according to the method of manufacturing a clip comprising the steps of:
forming the precursor of a clip from a material comprising a superelastic alloy which has an austenitic state and a martensitic state, said precursor having a substantially annular body which is substantially planar and having a plurality of tines which extend radially outwardly from said body;
inverting said precursor such that said tines extend radially inwardly and said precursor is in a substantially planar configuration;
heating said precursor in its inverted configuration to cause said alloy to become substantially austenitic; and
quenching said heated precursor to form a clip which is substantially austenitic in the substantially planar configuration with at least two tines being in a parallel side-by-side relationship in the substantially planar configuration and extending past each other beyond a central axis of the clip, the central axis of the clip being perpendicular to a plane formed by the clip in the substantially planar configuration.

12. The clip of claim 11 wherein said alloy is nickel-titanium.

13. The clip of claim 11 wherein said body comprises a plurality of looped elements.

14. The clip of claim 11 wherein said forming step comprises cutting said precursor from a sheet of material comprising a superelastic alloy.

15. The clip of claim 11 wherein at least one tine is longer than a radially opposed tine.

* * * * *